(12) United States Patent
Kurono et al.

(10) Patent No.: US 8,738,182 B2
(45) Date of Patent: May 27, 2014

(54) SAMPLE PROCESSING APPARATUS

(71) Applicant: Sysmex Corporation, Kobe (JP)

(72) Inventors: Hiroshi Kurono, Kobe (JP); Daiki Karino, Kobe (JP)

(73) Assignee: Sysmex Corporation, Kobe-shi (JP)

(*) Notice: Subject to any disclaimer, the term of this patent is extended or adjusted under 35 U.S.C. 154(b) by 0 days.

(21) Appl. No.: 13/629,310

(22) Filed: Sep. 27, 2012

(65) Prior Publication Data
US 2013/0084212 A1    Apr. 4, 2013

(30) Foreign Application Priority Data

Sep. 30, 2011  (JP) .................................. 2011-218039

(51) Int. Cl.
*G05B 21/00* (2006.01)
(52) U.S. Cl.
USPC .......................................................... 700/266
(58) Field of Classification Search
USPC .......................................... 700/266, 275, 302
See application file for complete search history.

(56) References Cited

U.S. PATENT DOCUMENTS

2005/0123445 A1   6/2005   Blecka et al.
2006/0177344 A1*  8/2006   Ouchi et al. .................... 422/64

FOREIGN PATENT DOCUMENTS

| CN | 1818660 A | 8/2006 |
|---|---|---|
| JP | 6-3361 A | 1/1994 |
| JP | 2009-287997 | 12/2009 |
| JP | 2010-190844 A | 9/2010 |

* cited by examiner

*Primary Examiner* — Natalia Levkovich
(74) *Attorney, Agent, or Firm* — Sughrue Mion, PLLC

(57) ABSTRACT

A sample processing apparatus includes: a sample processing unit comprising a moving mechanism and configured to perform a sample processing operation by moving the moving mechanism; a cover configured to cover the moving mechanism of the sample processing unit; a lock mechanism configured to lock the cover to prevent the cover from being opened; and a controller configured to control the lock mechanism, wherein the controller is configured to set either of a first mode and a second mode, wherein in the first mode, the cover is kept locked after the sample processing unit has completed the sample processing operation until an instruction to unlock the cover is received from a user, and in the second mode, the cover is automatically unlocked after the sample processing unit has completed the sample processing operation.

16 Claims, 17 Drawing Sheets

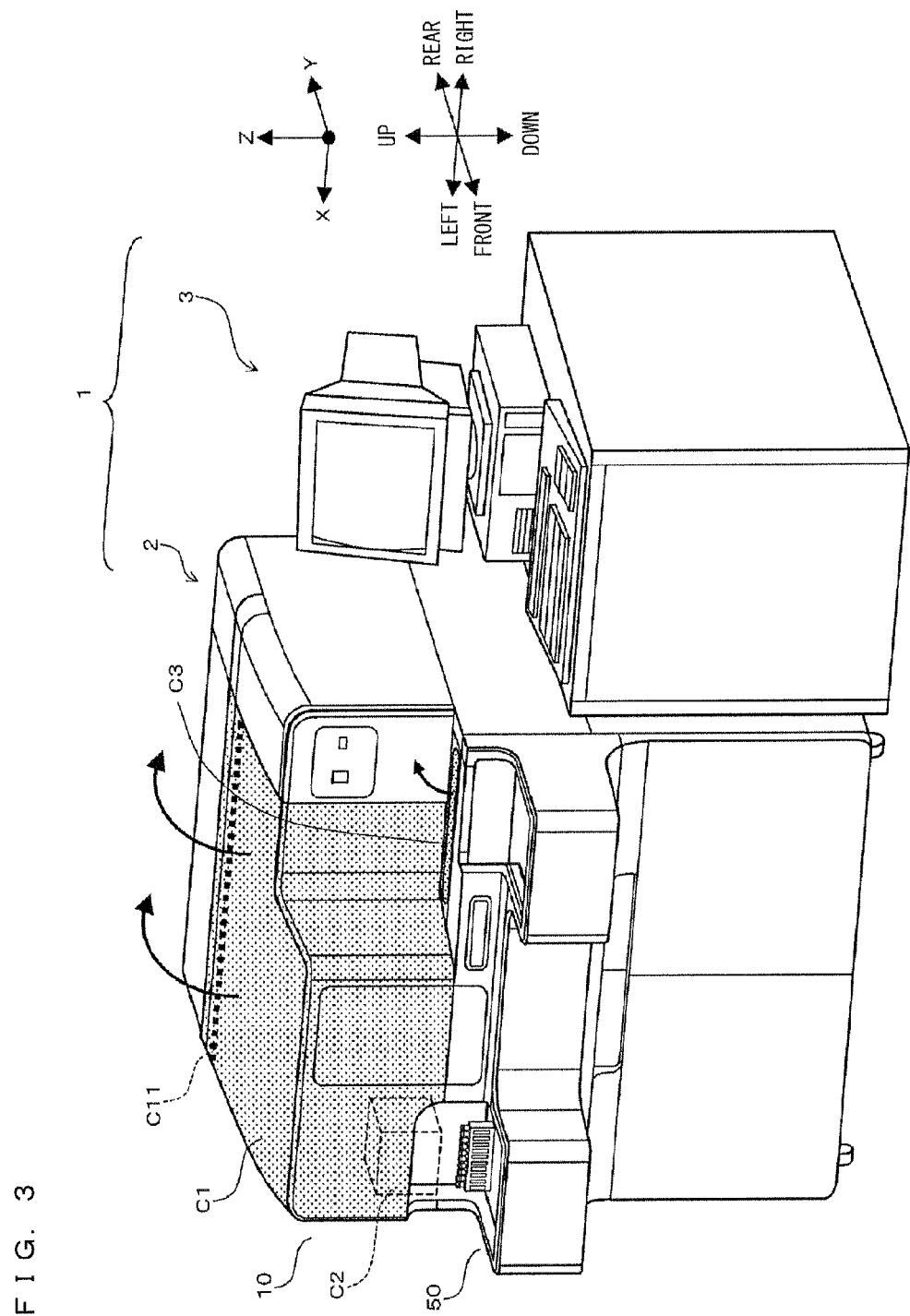

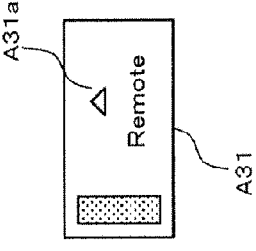
FIG. 8A
| MODE | STATE |
|---|---|
| LOCAL CHANGEABLE | MEASURE |
| | SUSPEND |
| | STANDBY |
| LOCAL FIXED | MEASURE |
| | SUSPEND |
| | STANDBY |
| REMOTE | MEASURE |
| | SUSPEND |
| | WAIT |
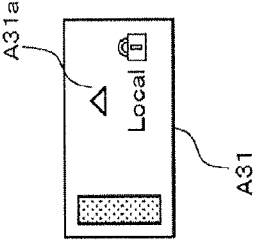
FIG. 8B
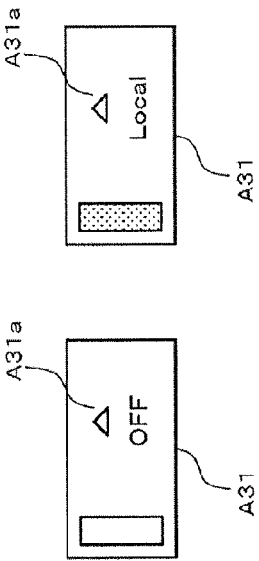
FIG. 8C
FIG. 8D
FIG. 8E
FIG. 8F

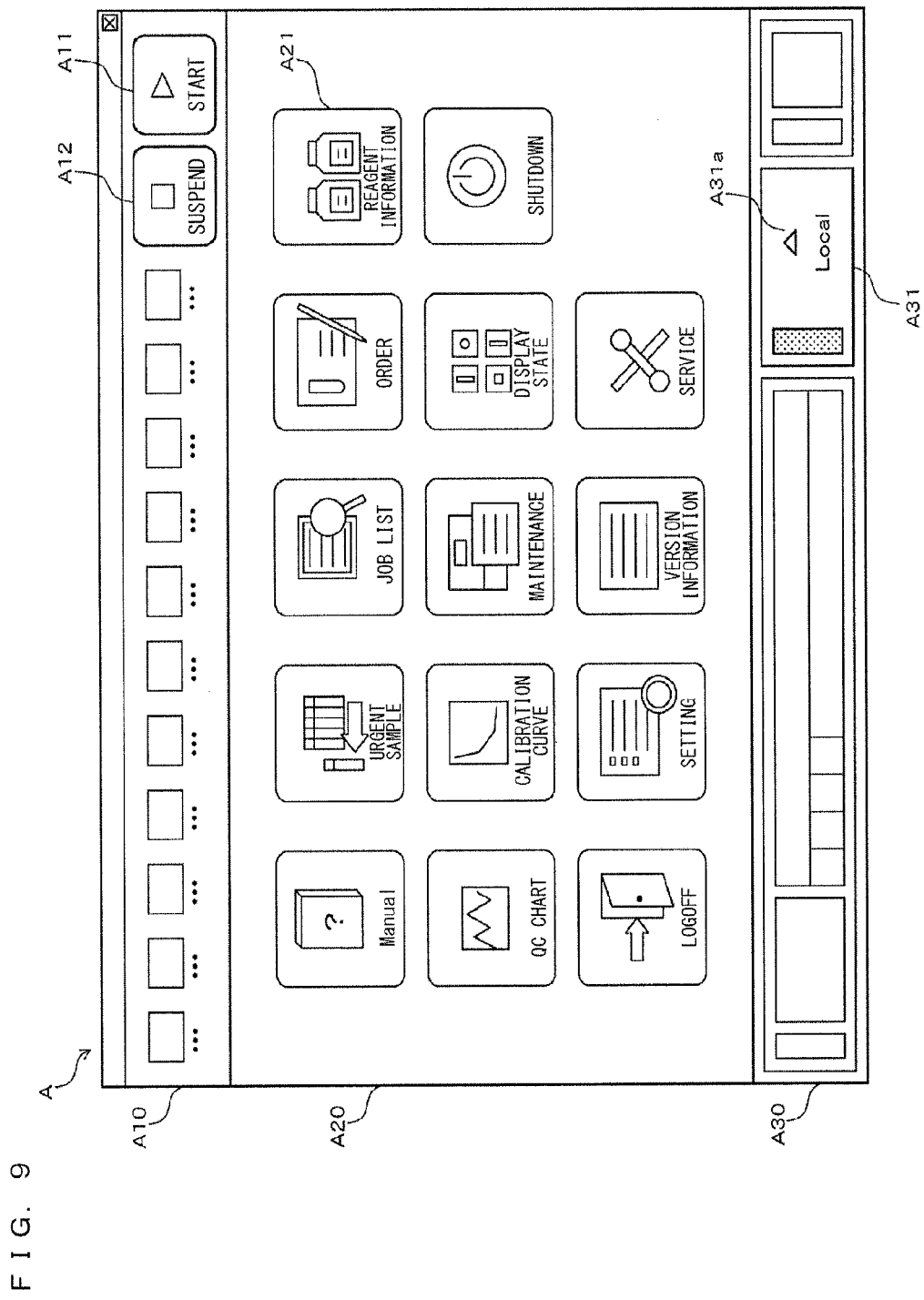

FIG. 10A
CONDITION FOR SHIFTING TO STANDBY

| 1 | NO SAMPLE BEING MEASURED |
| 2 | NO SAMPLE IN CUVETTE TABLE 13 |
| 3 | NO SAMPLE RACK L IN RACK SET REGION 51 AND TRANSPORTATION REGION 52 |

FIG. 10B
CONDITION FOR SHIFTING TO WAIT

| 1 | NO SAMPLE BEING MEASURED |
| 2 | NO SAMPLE IN CUVETTE TABLE 13 |
| 3 | NO SAMPLE RACK L IN RACK SET REGION 51 AND TRANSPORTATION REGION 52 |
| 4 | NO TRANSPORTED SAMPLE THAT IS NOT ASPIRATED YET |

FIG. 10C
PROCESS FOR SHIFTING TO STANDBY

| 1 | TURN OFF PNEUMATIC SOURCE 213 |
| 2 | WITHDRAW ARMS OF DISPENSING UNITS 21 TO 25 |
| 3 | MOVE DILUENT TRANSPORTER 16 UNDER DILUENT COVER C3 |
| 4 | UNLOCK COVER OF DILUENT COVER C3 |

FIG. 10D
PROCESS FOR SHIFTING TO WAIT

| 1 | TURN OFF PNEUMATIC SOURCE 213 |
| 2 | WITHDRAW ARMS OF DISPENSING UNITS 21 TO 25 |
| 3 | MOVE DILUENT TRANSPORTER 16 UNDER DILUENT COVER C3 |

FIG. 10E
CONDITION FOR CANCELING STANDBY

| 1 | START BUTTON A11 IS PRESSED |

FIG. 10F
CONDITION FOR CANCELING WAIT

| 1 | START BUTTON A11 IS PRESSED |
| 2 | SAMPLE RACK L IS PLACED IN RACK SET REGION 51 |
| 3 | SAMPLE CONTAINER T HAS ARRIVED AT TRANSPORTATION LINE |

FIG. 10G
PROCESS FOR CANCELING STANDBY

| 1 | TURN ON PNEUMATIC SOURCE 213 |
| 2 | INITIALIZE ARM POSITIONS OF DISPENSING UNITS 21 TO 25 |
| 3 | WASH PIPETTES OF DISPENSING UNITS 21 TO 25 WITH WATER |
| 4 | INITIALIZE POSITIONS OF REAGENT TABLES 11 AND 12 |
| 5 | INITIALIZE TRANSPORTATION UNIT 50 |
| 6 | INITIALIZE BAR CODE READER 54 |
| 7 | INITIALIZE CUVETTE TABLE 13 AND HEATING TABLE 14 |
| 8 | INITIALIZE CATCHER UNITS 27 AND 28 |
| 9 | DISCARD CUVETTE REMAINING IN HEATING TABLE 14 |

FIG. 10H
BASIC CANCELLING PROCESS

| 1 | TURN ON PNEUMATIC SOURCE 213 |
| 2 | INITIALIZE ARM POSITIONS OF DISPENSING UNITS 21 TO 25 |
| 3 | WASH PIPETTES OF DISPENSING UNITS 21 TO 25 WITH WATER |

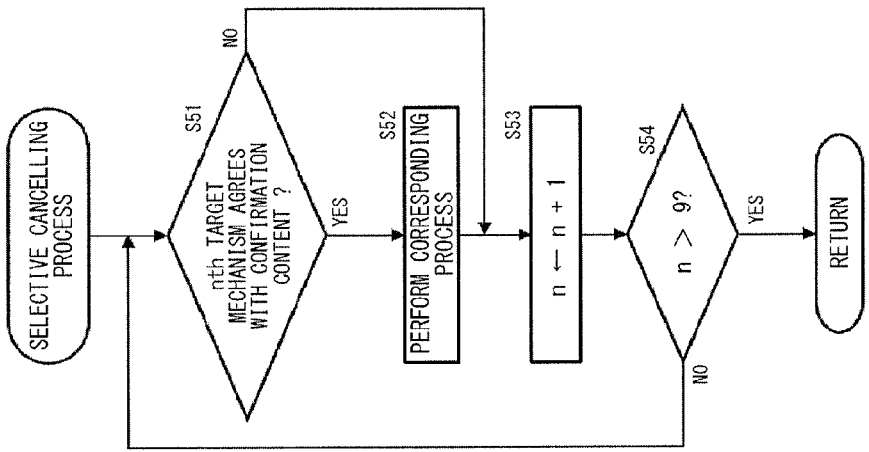

F I G. 14B

F I G. 14A

| | TARGET MECHANISM | CONFIRMATION CONTENT | PROCESSING CONTENT |
|---|---|---|---|
| 1 | REAGENT TABLES 11 AND 12 | MOVED ? | MOVE TO ORIGINAL POSITION |
| 2 | CUVETTE TABLE 13 | MOVED ? | MOVE TO ORIGINAL POSITION |
| 3 | HEATING TABLE 14 | MOVED ? | MOVE TO ORIGINAL POSITION |
| 4 | CATCHER UNIT 26 | MOVED ? | MOVE TO ORIGINAL POSITION |
| 5 | CATCHER UNIT 27 | MOVED ? | MOVE TO ORIGINAL POSITION |
| 6 | CATCHER UNIT 28 | MOVED ? | MOVE TO ORIGINAL POSITION |
| 7 | CUVETTE ON HEATING TABLE 14 | REMAINING ? | DISCARD |
| 8 | TRANSPORTATION UNIT 50 | MOVED ? | MOVE TO ORIGINAL POSITION |
| 9 | BAR CODE READER 54 | MOVED ? | MOVE TO ORIGINAL POSITION |

SAMPLE PROCESSING APPARATUS

FIELD OF THE INVENTION

The present invention relates to a sample processing apparatus configured to perform predetermined processing on samples such as blood and urine.

BACKGROUND

For example, Japanese Laid-Open Patent Publication No. H6-3361 and Japanese Laid-Open Patent Publication No. 2010-190844 disclose an automatic analysis system which is provided with a transportation line configured to transport samples to a plurality of apparatuses, and which perform analytical operations on the samples by transporting the samples to the apparatuses by the transportation line. Typically, a sample processing apparatus connected to such transportation line is provided with a cover which covers a moving mechanism in the apparatus, and the cover is configured to be openable and closable so as to allow a user to perform reagent replacement, maintenance, and the like.

In the case where the above sample processing apparatus is connected to a transportation line, the transportation line transports samples to the sample processing apparatus at irregular time intervals in accordance with the timings at which sample processing in other apparatuses ended. Accordingly, the operation of the sample processing apparatus is often suspended. While the sample processing operation is being suspended, a user may carelessly touch a moving mechanism in the sample processing apparatus and displace it. If the sample processing operation is resumed when the moving mechanism has been displaced, the apparatus may not be able to locate the moving mechanism at its intended position. Therefore, every time a sample is transported to the sample processing apparatus by the transportation line, the sample processing apparatus needs to perform operations such as detecting whether the cover has been opened or not and returning the moving mechanism to its original position. This makes it difficult to smoothly process samples.

SUMMARY

The scope of the present invention is defined solely by the appended claims, and is not affected to any degree by the statements within this summary.

A first aspect of the present invention is a sample processing apparatus for processing a sample, comprising: a sample processing unit comprising a moving mechanism and configured to perform a sample processing operation by moving the moving mechanism; a cover configured to cover the moving mechanism of the sample processing unit; a lock mechanism configured to lock the cover to prevent the cover from being opened; and a controller configured to control the lock mechanism, wherein the controller is configured to set either of a first mode and a second mode, wherein in the first mode, the cover is kept locked after the sample processing unit has completed the sample processing operation until an instruction to unlock the cover is received from a user, and in the second mode, the cover is automatically unlocked after the sample processing unit has completed the sample processing operation.

A second aspect of the present invention is a sample processing apparatus connectable to a transportation line which transports a sample to a plurality of sample processing apparatuses, comprising: a sample processing unit comprising a moving mechanism and configured to perform a sample processing operation by moving the moving mechanism; a cover configured to cover the moving mechanism of the sample processing unit; a lock mechanism configured to lock the cover to prevent the cover from being opened; and a controller configured to control the lock mechanism, wherein the controller controls the moving mechanism so as to perform an operation of processing a sample transported by the transportation line, locks the cover during the operation of processing the sample, and keeps the cover locked after the operation of processing the sample has been completed until an instruction to unlock the cover is received from a user.

BRIEF DESCRIPTION OF THE DRAWINGS

FIG. 3 is an external view showing a configuration of a sample analyzer according to an embodiment;

FIG. 8A shows modes and states of a sample analyzer according to an embodiment, FIG. 8B shows a local mode changing screen, and FIG. 8C to 8F each show a content displayed in a mode display area;

FIG. 9 shows a menu screen displayed on a display unit of an information processing apparatus according to an embodiment;

FIG. 10A shows a "condition for shifting to standby" according to an embodiment, FIG. 10B shows a "condition for shifting to wait", FIG. 10C shows a "process for shifting to standby", FIG. 10D shows a "process for shifting to wait", FIG. 10E shows a "condition for canceling standby", FIG. 10F shows a "condition for canceling wait", FIG. 10G shows a "process for canceling standby", and FIG. 10H shows a basic cancelling process;

FIG. 14A illustrates a content of a "selective cancelling process" according to an embodiment, and FIG. 14B is a flow chart showing the "selective cancelling process";

DETAILED DESCRIPTION OF THE EMBODIMENT

The present embodiment is realized by applying the present invention to a sample analyzer for performing tests and analyses regarding blood.

Hereinafter, a sample analyzer according to the present embodiment will be described with reference to the drawings.

Figure 1:
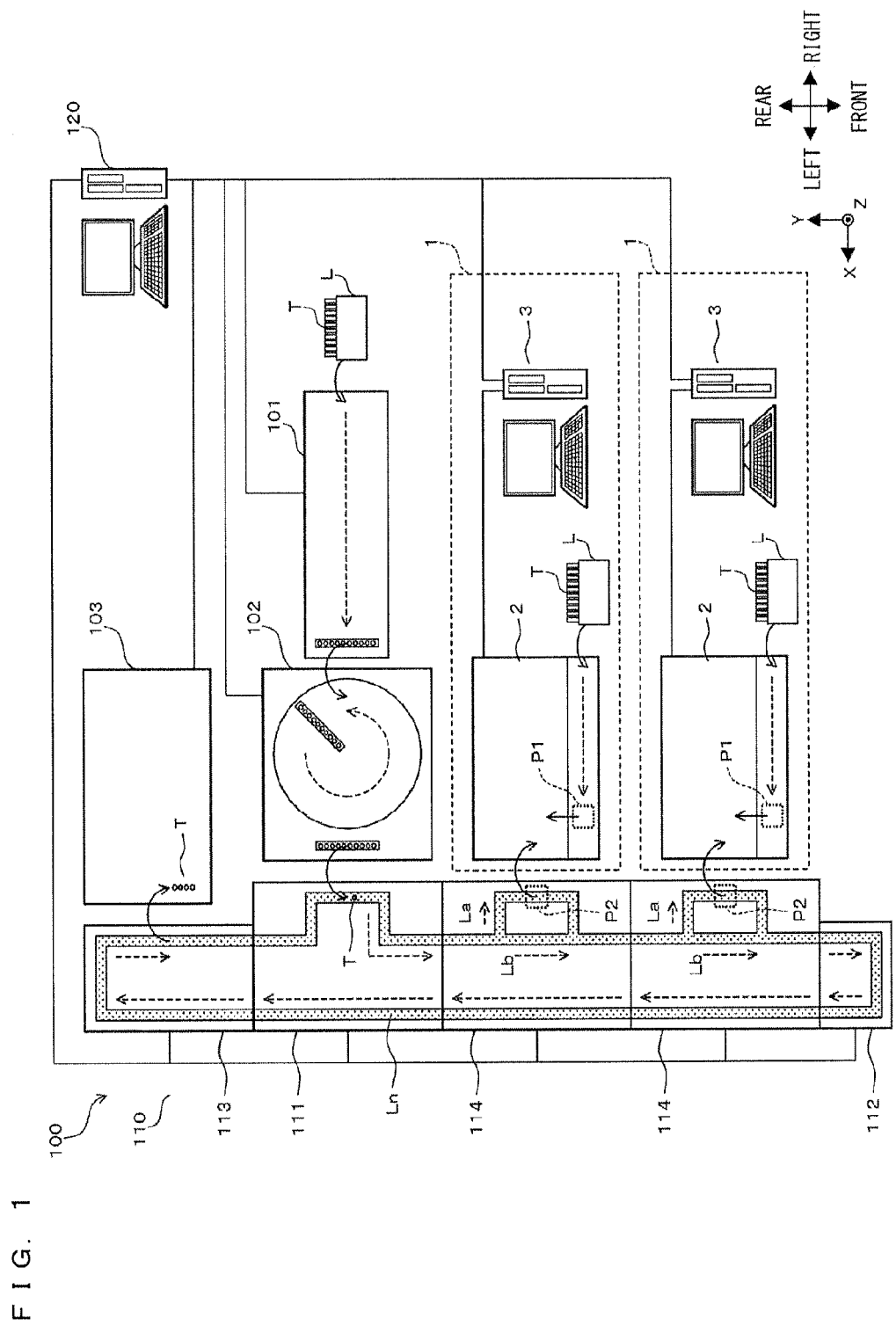
FIG. 1 is a plan view showing a configuration of a sample processing system according to an embodiment, viewed from above.

FIG. 1 is a plan view showing a configuration of a sample processing system 100 including a sample analyzer 1, viewed from above.

The sample analyzer 1 is a blood coagulation analyzer that performs an optical measurement and an analysis of a sample, using a coagulation method, a synthetic substrate method, immunonephelometry, and an aggregation method, by illuminating a measurement specimen prepared by adding reagents to the sample (plasma). The sample analyzer 1 includes a measurement apparatus 2 which optically measures components included in a sample (plasma), and an information processing apparatus 3 which analyzes measurement data obtained by the measurement apparatus 2 and issues operation instructions to the measurement apparatus 2. The measurement apparatus 2 and the information processing apparatus 3 are communicably connected to each other.

The sample processing system 100 includes a rack set apparatus 101, a centrifuge 102, a container storing apparatus 103, two sample analyzers 1, a transportation system 110, and a transportation controller 120. The transportation system 110 includes transportation units 111 to 113, and two transportation units 114. The centrifuge 102 and the container storing apparatus 103 are arranged to the right of the transportation units 111 and 113, respectively. The sample analyzers 1 are arranged to the right of the transportation units 114, respectively.

When performing measurement of a sample contained in a sample container T, a user sets the sample container T in a sample rack L and sets this sample rack L in the measurement apparatus 2 or the rack set apparatus 101. In the present embodiment, in either case where the sample rack L is set in the measurement apparatus 2 or in the rack set apparatus 101, it is possible to start measurement of the sample in the sample container T accommodated in the sample rack L.

Figure 2A:
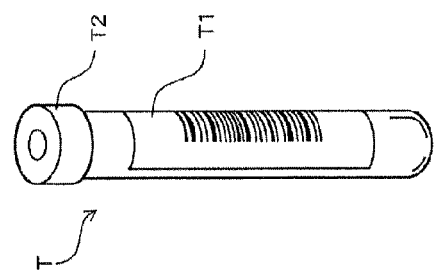
FIG. 2A shows a configuration of a sample container according to an embodiment.
Figure 2B:
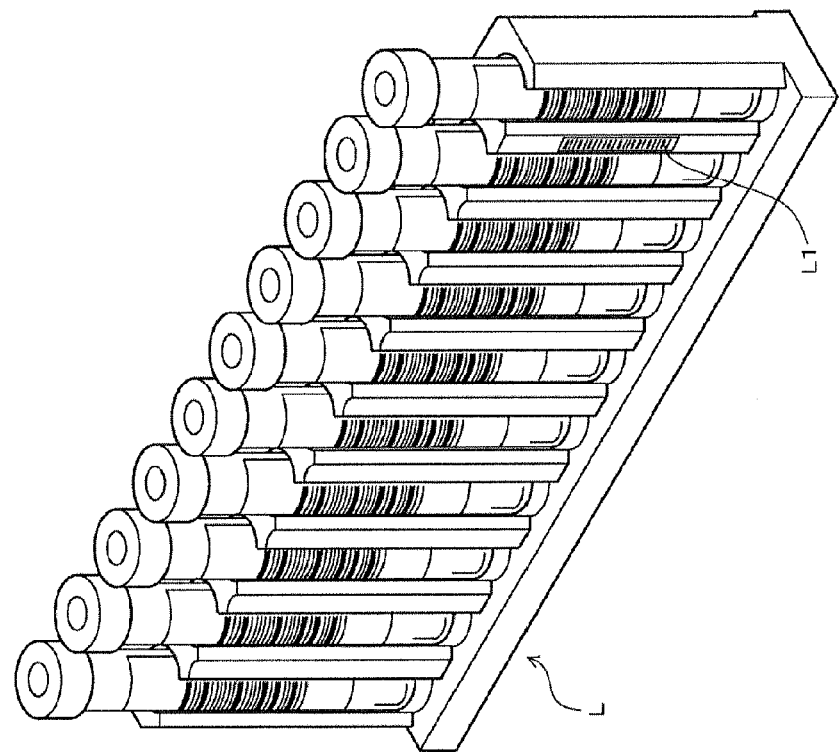
FIG. 2B shows a configuration of a sample rack according to an embodiment.

FIG. 2A and FIG. 2B show configurations of a sample container T and a sample rack L, respectively.

With reference to FIG. 2A, the sample container T is a tubular container which is formed of translucent glass or translucent synthetic resin, and whose upper end is open. A bar code label T1 is affixed to a lateral side of the sample container T. A bar code representing a sample ID is printed on the bar code label T1. The sample container T contains a blood sample collected from a patient, and its upper end opening is sealed with a lid T2.

With reference to FIG. 2B, the sample rack L is provided with an accommodation part capable of vertically accommodating ten sample containers T therein. A bar code label L1 is affixed to a lateral side of the sample rack L. A bar code representing a rack ID is printed on the bar code label L1.

With reference back to FIG. 1, when a sample rack L is set in a measurement apparatus 2, the sample rack L is transported within the measurement apparatus 2, and the sample containers T are sequentially located at an aspirating position P1. When a sample container T is located at the aspirating position P1, the sample is aspirated from the sample container T, and measurement of the sample is performed in the measurement apparatus 2.

On the other hand, when a sample rack L is set in the rack set apparatus 101, the sample rack L is transported leftward by the rack set apparatus 101 to be set in the centrifuge 102 which is located to the left of the rack set apparatus 101. The sample rack L set in the centrifuge 102 is centrifuged by the centrifuge 102, and then located in a left end portion of the centrifuge 102.

The transportation units of the transportation system 110 include a loop transportation line Ln for transporting sample containers T along the broken-line direction in the transportation system 110. Each sample container T is independently transported along the transportation line Ln, accommodated in a container accommodating part 130 (see FIG. 5). Each sample container T accommodated in the sample rack L located at the left end portion of the centrifuge 102 is set in a container accommodating part 130 on the transportation line Ln of the transportation unit 111, and transported on the transportation line Ln toward a transportation unit 114.

The sample container T transported from the transportation unit 111 to the rear-side transportation unit 114 is transported to a transportation line La or a transportation line Lb, respectively, in accordance with whether measurement of the sample is to be performed or not in the sample analyzer 1 that is located to the right of this transportation unit 114. In other words, when measurement of the sample is to be performed in the sample analyzer 1, the sample container T is transported to the transportation line La to be located at an aspirating position P2. When the sample container T is located at the aspirating position P2, the sample is aspirated from the sample container T, and measurement of the sample is performed in the measurement apparatus 2. When measurement of the sample is not performed in the sample analyzer 1, the sample container T is transported to the transportation line Lb, and is transported toward the transportation unit located to the front of this rear-side transportation unit 114.

Also with respect to the sample container T transported from the read-side transportation unit 114 to the front-side transportation unit 114, processes similar to those described above are performed in the front-side transportation unit 114 and in the sample analyzer 1 that is located to the right of this transportation unit 114.

The sample container T transported from the front-side transportation unit 114 to the transportation unit 112 is transported rearward on the transportation line Ln. The sample container T transported from the transportation unit 111 to the transportation unit 113 is taken out at a predetermined position to be stored in the container storing apparatus 103.

The transportation controller 120 is communicably connected to the rack set apparatus 101, the centrifuge 102, the container storing apparatus 103, each of the two sample analyzers 1, and each of the transportation units of the transportation system 110. The transportation controller 120 controls operations of the rack set apparatus 101, the centrifuge 102, the container storing apparatus 103, and the transportation system 110. Moreover, the transportation controller 120 transmits, to the two sample analyzers 1, transportation statuses of sample containers T in the transportation system 110.

FIG. 3 is an external view showing a configuration of the sample analyzer 1.

The measurement apparatus 2 includes a measurement unit 10 which performs measurement of samples, and a transportation unit 50 for transporting sample racks L. Moreover, the measurement apparatus 2 is provided with a body cover C1 which covers moving mechanisms in the measurement unit 10, a lock mechanism C2 provided in the measurement unit 10, and a diluent cover C3 which covers a diluent replacement position P3 (see FIG. 5).

The lock mechanism C2 is arranged inside the body cover C1 and near the front left of the measurement unit 10. The body cover C1 enters a locked state or an unlocked state by means of the lock mechanism C2. When the body cover C1 is in the unlocked state, the user can open the body cover C1 upwardly using a shaft C11 as an axis for rotation to access mechanisms of the measurement unit 10. Accordingly, the user can perform replacement of a reagent container in the measurement unit 10 or maintenance of the inside of the measurement unit 10.

The diluent cover C3 enters a locked state or an unlocked state by means of a lock mechanism not shown. When the diluent cover C3 is in the unlocked state, the user can open the diluent cover C3 upwardly to access the diluent replacement position P3. Accordingly, without opening the body cover C1, the user can replace a diluent container accommodated in a diluent transporter 16 (see FIG. 5) located at the diluent replacement position P3.

Figure 4A:
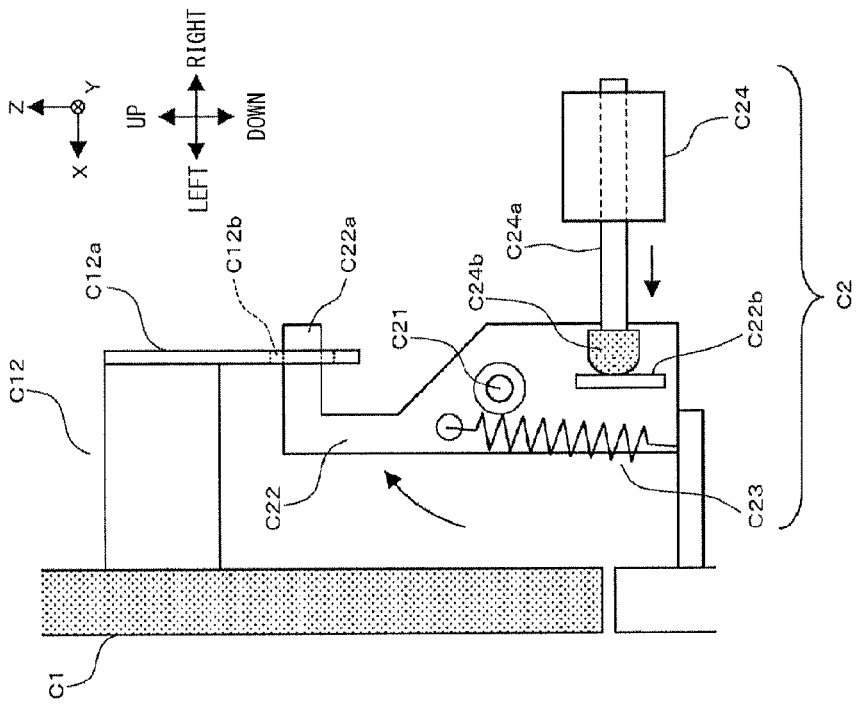
FIG. 4A illustrates how a body cover enters an unlocked state by means of a lock mechanism according to an embodiment.
Figure 4B:
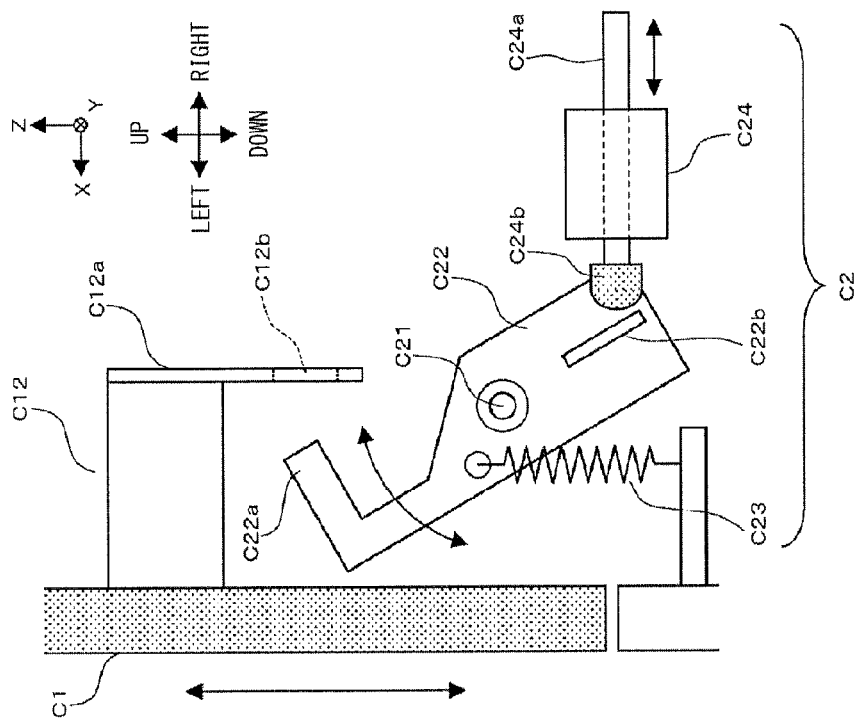
FIG. 4B illustrates how the body cover enters a locked state by means of the lock mechanism.

FIGS. 4A and 4B illustrate how the body cover C1 enters an unlocked state and a locked state, respectively, by means of the lock mechanism C2. FIG. 4A is a side view of the body cover C1 in the unlocked state, and FIG. 4B is a side view of the body cover C1 in the locked state.

A support C12 is provided, inside the body cover C1, at a front portion of the left lateral side of the body cover C1. A flange C12a extending parallel to the Y-Z plane is formed at the right end of the support C12. A hole C12b passing through the flange C12a in the X-axis direction is formed near the lower end of the flange C12a.

The lock mechanism C2 includes a shaft C21, an engaging plate C22, a spring C23, and a motor C24. The shaft C21 extends in the Y-axis direction and is arranged within the measurement apparatus 2. The engaging plate C22 is supported by the shaft C21 so as to be able to rotate, in the X-Z plane, about the shaft C21. An L-shaped engagement part C22a is formed in an upper end portion of the engaging plate C22, and a flange C22b having a plane parallel to the Y-axis is formed near a lower end portion of the engaging plate C22. The lower end of the spring C23 is fixed within the measurement apparatus 2, and the upper end of the spring C23 is fixed to the engaging plate C22. The motor C24 includes a shaft C24a extending in the X-axis direction, and a pushing member C24b is provided at the left end of the shaft C24a.

FIG. 4A illustrates a state of the body cover C1 immediately after it has just been closed. At this time, the pushing member C24b is not contacting the flange C22b and the engaging plate C22 is being pulled by the spring C23. Accordingly, the engagement part C22a is inclined leftward, and the body cover C1 is in an unlocked state.

Here, if the motor C24 is driven to move the shaft C24a leftward, the pushing member C24b contacts the flange C22b, and the engaging plate C22 rotates about the shaft C21, i.e., about the Y-axis, against a tension applied by the spring C23. As a result, the engagement part C22a moves rightward, and inserted into the hole C12b as shown in FIG. 4B. In this manner, the body cover C1 enters a locked state, and the user cannot open the body cover C1 any more.

While the body cover C1 is in a locked state, when the motor C24 is driven to move the shaft C24a rightward, the engaging plate C22 is pulled by the spring C23 and inclined leftward as shown in FIG. 4A. As a result, the body cover C1 enters an unlocked state, and now the user can open the body cover C1. It should be noted that the diluent cover C3 is also provided with a lock mechanism similar to that for the body cover C1.

Figure 5:
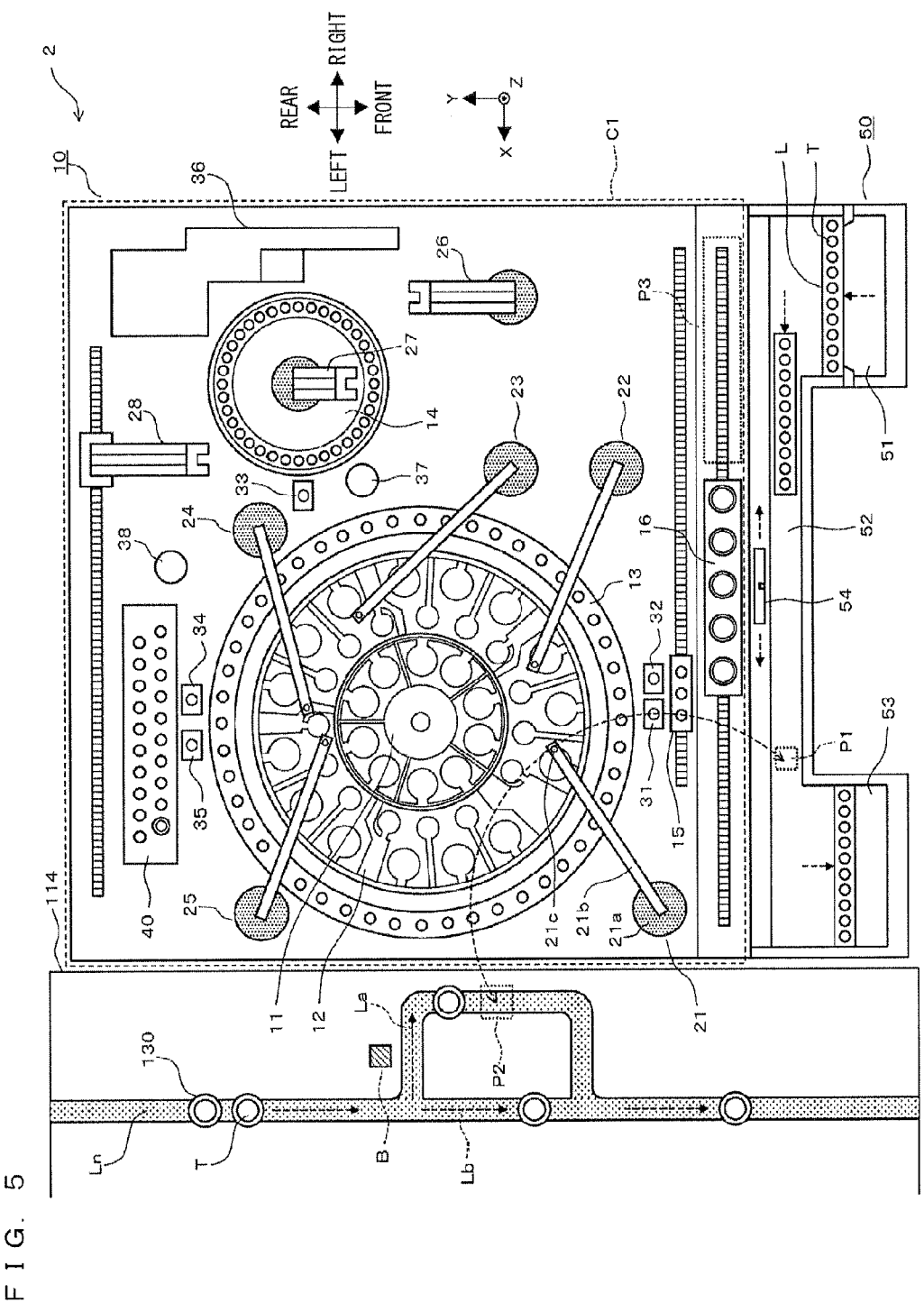
FIG. 5 is a plan view of a measurement apparatus and a transportation unit according to an embodiment, viewed from above.

FIG. 5 is a plan view of the measurement apparatus 2 and the transportation unit 114, viewed from above. FIG. 5 illustrates them as seeing through the body cover C1.

As shown in FIG. 5, reagent tables 11 and 12, a cuvette table 13, a heating table 14, a cuvette transporter 15, the diluent transporter 16, dispensing units 21 to 25, catcher units 26 to 28 (hereinafter, collectively referred to as "moving mechanism group") are provided inside the body cover C1 of the measurement unit 10. When the body cover C1 is in a locked state, the user cannot access the moving mechanism group, and when the body cover C1 is in an unlocked state, the user can access the moving mechanism group by opening the body cover C1, and can move the moving mechanism group.

First, an operation of transporting a sample rack L performed by the transportation unit 50 will be described.

The transportation unit 50 is provided with a rack set region 51 on which sample racks L can be placed, a transportation region 52, a rack storing region 53 in which sample racks L transported from the transportation region 52 are stored so as to be taken out therefrom.

When it is detected that a sample rack L is set in the rack set region 51 based on a detection signal from a sensor (not shown) provided in the rack set region 51, the sample rack L on the rack set region 51 is sent to a right end portion of the transportation region 52.

The sample rack L located at the right end portion of the transportation region 52 is transported leftward along the transportation region 52, by a mechanism section (not shown) for transporting the sample rack L leftward and rightward. A bar code reader 54 movable leftward and rightward is provided near the center of the transportation region 52. The bar code reader 54 reads bar code labels T1 and a bar code label L1 respectively affixed to sample containers T and the sample rack L.

Also as shown in FIG. 1, the aspirating position P1 is set in the transportation region 52. The sample in a sample container T located at the aspirating position P1 is aspirated by the dispensing unit 21. When all of the samples in the sample containers T accommodated in the sample rack L are aspirated, the sample rack L is transported to a left end portion of the transportation region 52.

The sample rack L located in the left end portion of the transportation region 52 is sent forward to be stored in the rack storing region 53. Then, the operation of transporting the sample rack L ends. The transporting operation by the transportation unit 50 is performed for all sample racks L set in the rack set region 51.

Next, a sample measuring operation performed by the measurement unit 10 will be described.

The reagent tables 11 and 12 are each configured to be able to accommodate reagent containers and rotate. The cuvette table 13 and the heating table 14 are each configured to be able to accommodate cuvettes and rotate. The cuvette transporter 15 and the diluent transporter 16 are configured to be able to accommodate cuvettes and diluent containers, respectively, and to move leftward and rightward.

The dispensing unit 21 includes a support 21a, an arm 21b supported by the support 21a, and a pipette 21c. The support 21a is configured to be able to move upward and downward and to rotate. Accordingly, the pipette 21c attached to the tip of the arm 21b can move upward and downward, and can rotate about the support 21a. Each of the dispensing units 22 to 25 is also configured in the same manner as the dispensing unit 21. The catcher units 26 and 27 are each configured to be able to grip a cuvette, extend/contract, and rotate. The catcher unit 28 is configured to be able to grip a cuvette, extend/contract, and move leftward and rightward.

The sample in a sample container T located at the aspirating position P1 is aspirated by the pipette 21c of the dispensing unit 21, and discharged into a new cuvette set in the cuvette table 13. The dispensing unit 22 aspirates the sample in the cuvette set in the cuvette table 13, and discharges the sample into a new cuvette set in the cuvette transporter 15. Further, the dispensing unit 22 can aspirate a diluent in a diluent container set in the diluent transporter 16 and mix it into the sample.

It should be noted that new cuvettes supplied from a cuvette supply unit 36 are sequentially set to the cuvette table 13 and the cuvette transporter 15, by the catcher units 26 and 27, respectively.

After the sample is discharged into the cuvette set in the cuvette transporter 15, the cuvette transporter 15 is driven rightward and the cuvette is gripped by the catcher unit 26 to be set in the heating table 14. The cuvette set in the heating table 14 is heated by the heating table 14, and then set in a detection unit 40 by the catcher unit 27 or 28. At that time, a reagent in a reagent container accommodated in the reagent table 11 or the reagent table 12 is dispensed into the cuvette as appropriate by the dispensing unit 23 to 25.

The sample (measurement specimen) to which the reagents have been dispensed is subjected to processing performed by the detection unit 40, whereby optical information which reflects components contained in the measurement specimen is detected. Then, measurement of the sample ends. The cuvette for which the measurement ended and is no longer necessary is gripped by the catcher unit 27 or 28, and discarded into a disposal hole 37 or 38. The pipettes of the dispensing units 21 to 25 are put into washers 31 to 35 as appropriate to be washed with water.

In the present embodiment, as described above, it is possible to perform measurement on not only the sample in the sample container T located at the aspirating position P1 but also the sample in the sample container T located at the aspirating position P2.

With reference to a left portion of FIG. 5, a sample container T is transported, accommodated in a container accommodating part 130 that is transported along the transportation line Ln of the transportation unit 114. In the case where measurement is performed for a sample container T in the sample analyzer 1 corresponding to this transportation unit 114, the sample container T is transported along the transportation line La to be located to the front of a bar code reader B. The bar code reader B reads the sample ID from the bar code label T1 of the sample container T located to the front thereof. At this time, the transportation controller 120 transmits, along with the sample ID read by the bar code reader B, a command indicating that the sample container T has arrived at the bar code reader B to the information processing apparatus 3 of the corresponding sample analyzer 1.

Subsequently, the sample container T is located at the aspirating position P2. At this time, the transportation controller 120 transmits a command indicating that the sample container T has been located at the aspirating position P2 to the information processing apparatus 3 of the corresponding sample analyzer 1. The sample in the sample container T located at the aspirating position P2 is aspirated by the pipette 21c of the dispensing unit 21, as in the case of the sample container T located at the aspirating position P1, and discharged into a new cuvette set in the cuvette table 13. At this time, the information processing apparatus 3 transmits to the transportation controller 120 a command indicating that the sample has been aspirated from the sample container T at the aspirating position P2. Then, measurement is performed in the sample analyzer 1 also on the sample transported along the transportation line Ln.

Figure 6:
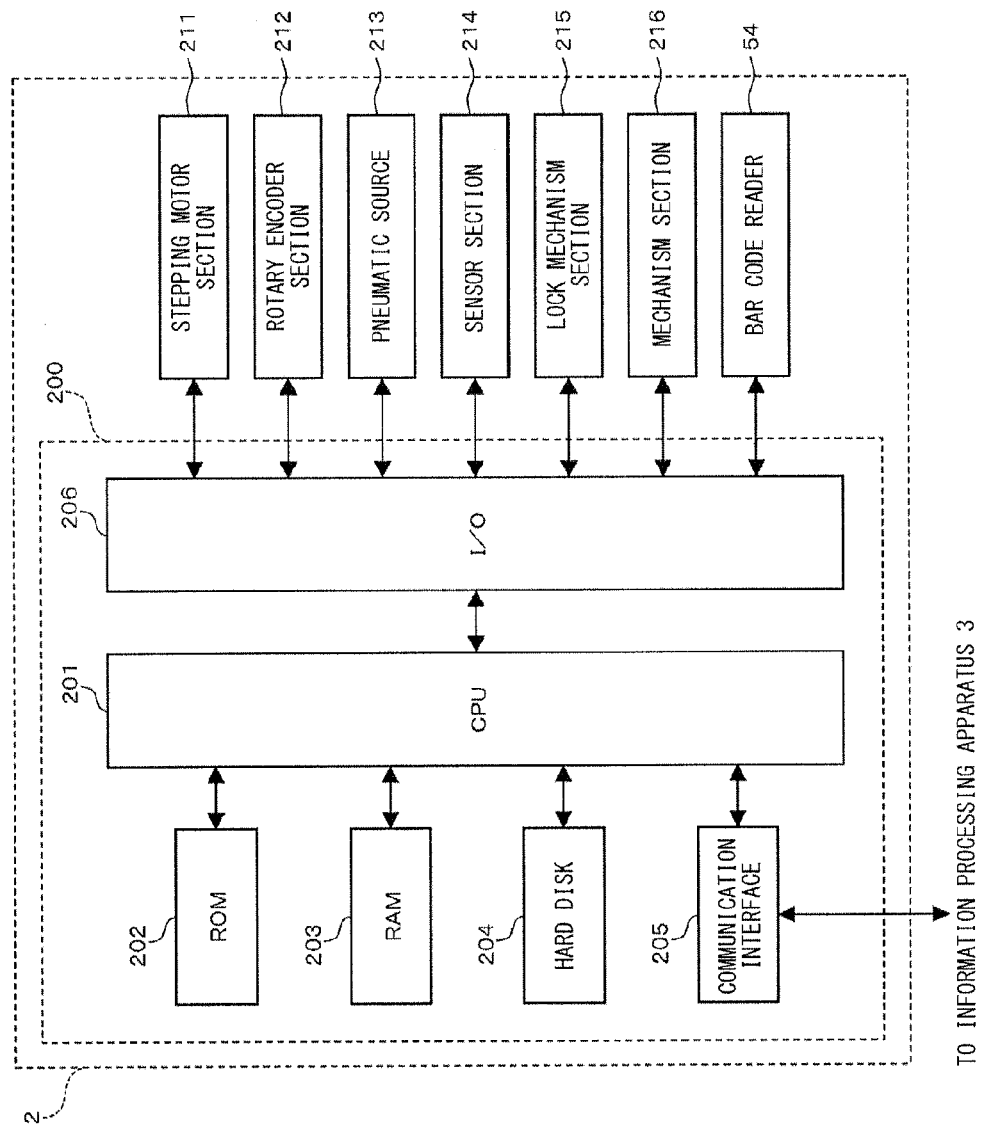
FIG. 6 shows a configuration of a measurement apparatus according to an embodiment.

FIG. 6 shows a configuration of the measurement apparatus 2.

The measurement apparatus 2 includes a controller 200, a stepping motor section 211, a rotary encoder section 212, a pneumatic source 213, a sensor section 214, a lock mechanism section 215, a mechanism section 216, and the bar code reader 54. The controller 200 includes a CPU 201, a ROM 202, a RAM 203, a hard disk 204, a communication interface 205, and an I/O interface 206.

The CPU 201 executes computer programs stored in the ROM 202 and computer programs loaded onto the RAM 203. The RAM 203 is used for reading computer programs stored in the ROM 202 and the hard disk 204. The RAM 203 is also used as a work area for the CPU 201 when these computer programs are executed.

Various computer programs to be executed by the CPU 201 such as an operating system and application programs, and data used for executing the computer programs are stored in the hard disk 204. The CPU 201 transmits/receives data to/from the information processing apparatus 3 via the communication interface 205.

The CPU 201 is connected, via the I/O interface 206, to the stepping motor section 211, the rotary encoder section 212, the pneumatic source 213, the sensor section 214, the lock mechanism section 215, the mechanism section 216, and the bar code reader 54. The CPU 201 receives signals from these mechanisms and controls them.

The stepping motor section 211 includes stepping motors for respectively driving the reagent tables 11 and 12, the cuvette table 13, the heating table 14, the cuvette transporter 15, the diluent transporter 16, the dispensing units 21 to 25, the catcher units 26 to 28, and mechanisms for moving a sample rack L on the transportation unit 50. The rotary encoder section 212 includes rotary encoders which respectively output pulse signals in accordance with the amounts of rotational displacements of the respective stepping motors included in the stepping motor section 211. Based on the number of pulses outputted from each rotary encoder included in the rotary encoder section 212, it is possible to detect the rotational amount of the corresponding stepping motor included in the stepping motor section 211.

The pneumatic source 213 supplies pressures to the dispensing units 21 to 25 so as to allow them to perform dispensing operations, respectively. The sensor section 214 includes original position sensors which detect whether mechanisms driven by the respective stepping motors in the stepping motor section 211 are located at their original positions, and various sensors for detecting sample racks L at predetermined positions on the transportation unit 50. When pipettes of the dispensing units 21 to 25 are located at positions over the washers 31 to 35, respectively, the dispensing units 21 to 25 are located at their original positions in their rotational directions.

The lock mechanism section 215 includes the lock mechanism C2 for switching the body cover C1 between a locked state and a unlocked state, and a lock mechanism for switching the diluent cover C3 between a locked state and a unlocked state. The mechanism section 216 includes a mechanism for washing with water the pipettes of the dispensing units 21 to 25 that are located over the washers 31 to 35, and other mechanism sections in the measurement apparatus 2 including the above moving mechanism group.

Figure 7:
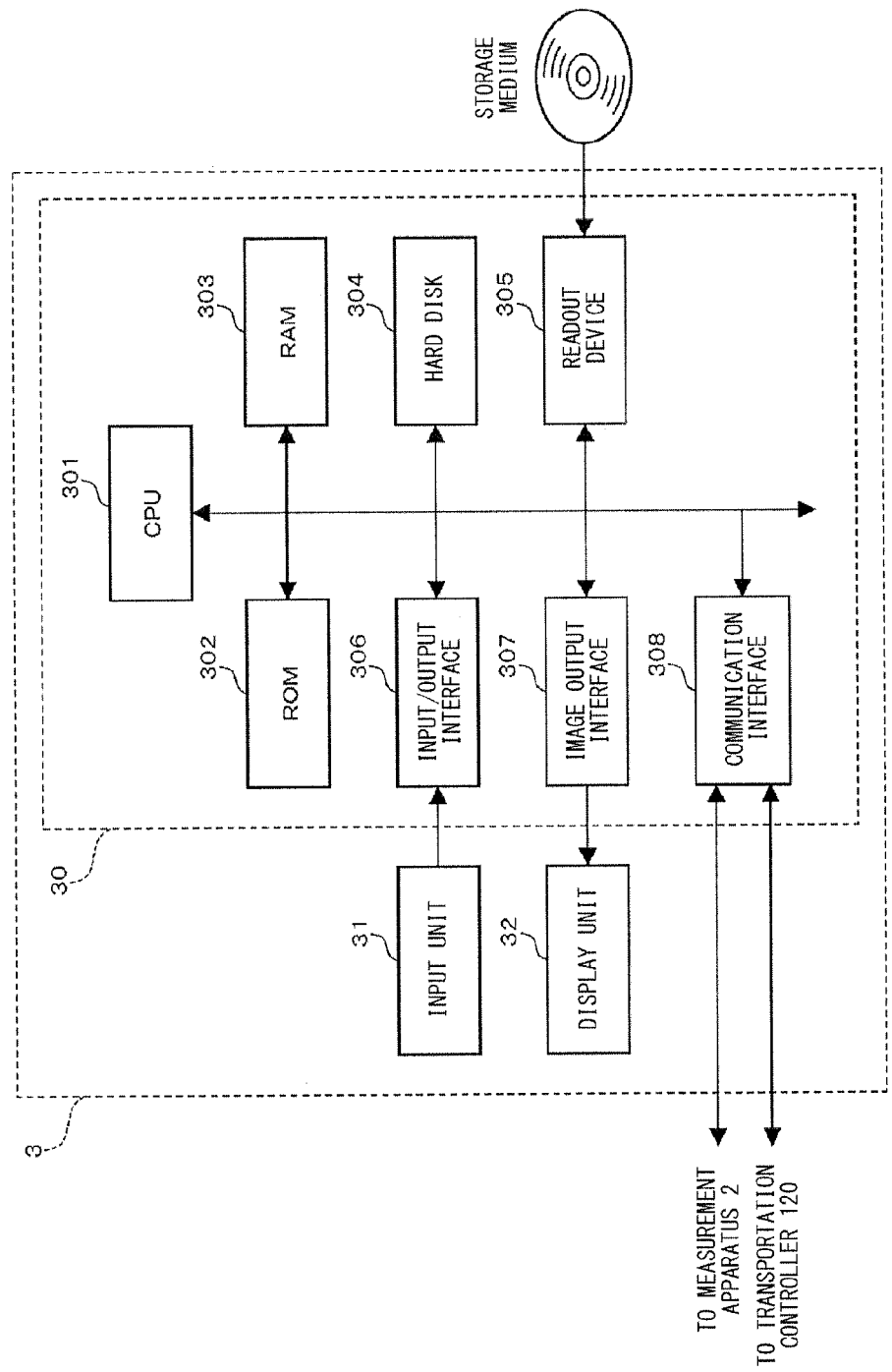
FIG. 7 shows a configuration of an information processing apparatus according to an embodiment.

FIG. 7 shows a configuration of the information processing apparatus 3.

The information processing apparatus 3 is implemented by a personal computer, and includes a body 30, an input unit 31, and a display unit 32. The body 30 includes a CPU 301, a ROM 302, a RAM 303, a hard disk 304, a readout device 305, an input/output interface 306, an image output interface 307, and a communication interface 308.

The CPU 301 executes computer programs stored in the ROM 302 and computer programs loaded onto the RAM 303. The RAM 303 is used for reading computer programs stored in the ROM 302 and the hard disk 304. The RAM 303 is also used as a work area for the CPU 301 when these computer programs are executed.

Various computer programs to be executed by the CPU 301 such as an operating system and application programs, and data used for executing the computer programs are stored in the hard disk 304.

The readout device 305 is implemented by a CD drive, a DVD drive, or the like, and is capable of reading computer programs and data stored in a storage medium. The input unit 31 composed of a mouse and a keyboard is connected to the input/output interface 306, and by a user using the input unit 31, an instruction and data are inputted to the information processing apparatus 3. The display unit 32 implemented by a display or the like is connected to the image output interface 307, and the image output interface 307 outputs video signals corresponding to image data to the display unit 32. The display unit 32 displays an image based on the inputted video signals. The communication interface 308 allows data transmission/reception to/from the measurement apparatus 2 and the transportation controller 120.

FIG. 8A shows modes and states of the sample analyzer 1.

For the sample analyzer 1, there are three modes: "local changeable", "local fixed", and "remote". For each of the modes "local changeable" and "local fixed" (hereinafter collectively referred to as "local"), there are three states: "measure", "suspend", and "standby". For the mode "remote", there are three states: "measure", "suspend", and "wait". The mode and the state of the sample analyzer 1 are stored in the hard disk 304 of the information processing apparatus 3.

In the sample analyzer 1, when the mode is "local", samples are sequentially aspirated from sample containers T each located at the aspirating position P1, and samples are not aspirated from sample containers T transported along the transportation line Ln of the transportation system 110. On the other hand, when the mode is "remote", in the sample analyzer 1, samples are sequentially aspirated from sample containers T each located at the aspirating position P1 and from sample containers T each located at the aspirating position P2.

While the mode is "local changeable", when the information processing apparatus 3 receives a remote request (a command indicating that a sample container T has arrived at the bar code reader B, and the sample ID thereof read by the bar code reader B) from the transportation controller 120 as described below, the mode is changed to "remote". While the mode is "local fixed", even when the information processing apparatus 3 receives the remote request from the transportation controller 120, the mode is not changed to "remote" and maintained at "local fixed".

When the state is "measure", a sample is aspirated from a sample container T located at the aspirating position P1 or the aspirating position P2 and measurement of the sample is performed in the measurement unit 10. When the state of the sample analyzer 1 becomes "suspend", operation of the measurement apparatus 2 is temporarily suspended. When the state becomes "standby" or "wait", the measurement apparatus 2 enters a predetermined state. "Standby" and "wait" will be described later with reference to FIGS. 10A to 10D.

FIG. 9 shows a menu screen A displayed on the display unit 32 of the information processing apparatus 3.

The menu screen A includes a toolbar area A10, an information display area A20, and a control area A30.

The toolbar area A10 includes a start button A11 and a suspension button A12, and is always displayed on the menu screen A. The start button A11 is a button for changing the state of the sample analyzer 1 to "measure" while the state thereof is "standby", "wait" or "suspend". The suspension button A12 is a button for changing the state of the sample analyzer 1 to "suspend" while the state thereof is "measure" or "wait".

Contents corresponding to operations designated in the toolbar area A10 and the control area A30 are displayed in the information display area A20. When a menu as shown in FIG. 9 is being displayed in the information display area A20, the information display area A20 includes a reagent information button A21. When replacing a reagent, the user presses the reagent information button A21 first, to cause a reagent information screen (not shown) to be displayed on the display unit 32. The user inputs, via the reagent information screen, an instruction to replace a reagent container accommodated in the reagent table 11 or 12 in the measurement unit 10. As a result, the state of the sample analyzer 1 becomes "suspend". This allows the user to open the body cover C1 to replace the reagent.

The control area A30 includes a mode display area A31 and is always displayed on the menu screen A. The mode display area A31 includes a button A31a, and indicates which of "local changeable", "local fixed" and "remote" is set as the mode of the sample analyzer 1. When the user presses the button A31a, a local mode changing screen A32 shown in FIG. 8B is displayed on the display unit 32.

With reference to FIG. 8B, the local mode changing screen A32 includes a checkbox A32a which is used when changing the mode from "remote" to "local fixed", or when changing the mode from "local fixed" to "local changeable". When the mode is "remote" or "local changeable", the checkbox A32a is unchecked, and when the mode is "local fixed", the checkbox A32a is checked. While the mode is "remote" or "local changeable", when the checkbox A32a that has been unchecked is checked and the OK button is pressed, the mode becomes "local fixed". While the mode is "local fixed", when the checkbox A32a that has been checked is unchecked and the OK button is pressed, the mode becomes "local changeable".

It should be noted that, when the mode is to be changed from "local changeable" to "remote", a remote request (a command indicating that a sample container T has arrived at the bar code reader B, and the sample ID thereof read by the bar code reader B) is transmitted to the sample analyzer 1 via the transportation controller 120. When the mode is to be changed from "local fixed" to "remote", the mode is firstly changed to "local changeable" via the local mode changing screen A32, and then, a remote request is transmitted to the sample analyzer 1 via the transportation controller 120.

Each of FIGS. 8C to 8F shows a content displayed in the mode display area A31.

When power supply to the measurement apparatus 2 is off, "OFF" is displayed in the mode display area A31 as shown in FIG. 8C. When the mode is "local changeable", "Local" is displayed in the mode display area A31 as shown in FIG. 8D. When the mode is "local fixed", "Local" and a key symbol are displayed in the mode display area A31 as shown in FIG. 8E.

When the mode is "remote", "Remote" is displayed in the mode display area A31 as shown in FIG. 8F.

FIG. 10A shows conditions (condition for shifting to standby) for shifting the state from "measure" to "standby" while the mode is "local". FIG. 10B shows conditions (condition for shifting to wait) for shifting the state from "measure" to "wait" while the mode is "remote".

With reference to FIG. 10A, when all of conditions 1 to 3 are satisfied, the state of the sample analyzer 1 is changed from "measure" to "standby". Condition 1 indicates a state where processing by the detection unit 40 has ended for all the samples that were aspirated by the dispensing unit 21. Condition 2 indicates a state where no cuvette containing a sample is accommodated in the cuvette table 13. Condition 3 indicates a state where it is determined that no sample rack L is present in the rack set region 51 and the transportation region 52, based on the sensor provided in the rack set region 51 and a transportation state of the mechanism section for transporting a sample rack L in the transportation region 52.

With reference to FIG. 10B, when all of conditions 1 to 4 are satisfied, the state of the sample analyzer 1 is changed from "measure" to "wait". Conditions 1 to 3 in FIG. 10B are the same as conditions 1 to 3 in FIG. 10A. Condition 4 indicates a state which is not a state where the sample in a sample container T whose sample ID was read by the bar code reader B of the corresponding transportation unit 114 has not been aspirated yet by the dispensing unit 21. In other words, condition 4 indicates a state where it is determined, based on a command transmitted from the transportation controller 120, that a sample container for which reading by the bar code reader B has ended does not exist between the bar code reader B and the aspirating position P2.

FIG. 10C shows processes (process for shifting to standby) performed when the state is to be shifted from "measure" to "standby" upon all the conditions in FIG. 10A being satisfied, and FIG. 10D shows processes (process for shifting to wait) performed when the state is to be shifted from "measure" to "wait" upon all the conditions in FIG. 10B being satisfied.

With reference to FIG. 10C, processes 1 to 4 are performed when the state is to be shifted from "measure" to "standby" upon all the conditions in FIG. 10A being satisfied. Process 1 indicates a process of turning off the drive of the pneumatic source 213. Process 2 indicates a process of rotating the arms of the dispensing units 21 to 25 such that the pipettes thereof are respectively located over the washers 31 to 35. Process 3 indicates a process of moving the diluent transporter 16 to a position under the diluent cover C3, that is, a process of locating the diluent transporter 16 at a rightmost portion in its left-right transportation range. Process 4 indicates a process of unlocking the diluent cover C3 by means of its corresponding lock mechanism.

With reference to FIG. 10D, processes 1 to 3 are performed when the state is to be shifted from "measure" to "wait" upon all the conditions in FIG. 10B being satisfied. Processes 1 to 3 in FIG. 10D are the same as processes 1 to 3 in FIG. 10C.

FIG. 10E shows a condition (condition for canceling standby) for shifting the state from "standby" to "measure" while the mode is "local", and FIG. 10F shows conditions (condition for canceling wait) for shifting the state from "wait" to "measure" while the mode is "remote".

With reference to FIG. 10E, when condition 1 is satisfied, the state of the sample analyzer 1 is changed from "standby" to "measure". Condition 1 indicates a state where the start button A11 shown in FIG. 9 has been pressed.

With reference to FIG. 10F, when any of conditions 1 to 3 is satisfied, the state of the sample analyzer 1 is changed from "wait" to "measure". Condition 1 in FIG. 10F is the same as condition 1 in FIG. 10E. Condition 2 indicates a state where it is determined, based on the sensor provided in the rack set region 51, that a sample rack L has been placed in the rack set region 51. Condition 3 indicates a state where the sample in a sample container T whose sample ID was read by the bar code reader B of the corresponding transportation unit 114 has not been aspirated yet by the dispensing unit 21. In other words, condition 3 indicates a state where a sample container T for which reading by the bar code reader B has ended exists between the bar code reader B and the aspirating position P2.

FIG. 10G shows processes (process for canceling standby) performed when the state is to be shifted from "standby" to "measure" upon the condition in FIG. 10E being satisfied, and FIG. 10H shows processes (basic cancelling process) that are always performed when the state is to be shifted from "wait" to "measure" upon any of the conditions in FIG. 10F being satisfied.

With reference to FIG. 10G, processes 1 to 9 are performed when the state is to be shifted from "standby" to "measure" upon the condition in FIG. 10E being satisfied. Process 1 indicates a process of turning on the drive of the pneumatic source 213. Process 2 indicates a process of initializing arm positions of the dispensing units 21 to 25, that is, a process in which rotational positions of the dispensing units 21 to 25 are located to their original positions based on their corresponding original position sensors. Process 3 indicates a process of washing with water the pipettes of the dispensing units 21 to 25 in the washers 31 to 35.

Process 4 indicates a process of initializing positions of the reagent tables 11 and 12, that is, a process in which rotational positions of the reagent tables 11 and 12 are located at their original positions based on their corresponding original position sensors. Process 5 indicates a process of initializing the transportation unit 50, that is, a process in which the mechanisms for moving a sample rack L on the transportation unit 50 are located at their original positions based on their corresponding original position sensors. Process 6 indicates a process of initializing the bar code reader 54, that is, a process in which the bar code reader 54 is located at its original position based on its corresponding original position sensor. Process 7 indicates a process of initializing the cuvette table 13 and the heating table 14, that is, a process in which the cuvette table 13 and the heating table 14 are located at their original positions based on their corresponding original position sensors. Process 8 indicates a process of initializing the catcher units 27 and 28, that is, a process in which the catcher units 27 and 28 are located at their original positions based on their corresponding original position sensors. Process 9 indicates a process of discarding all the cuvettes set in the heating table 14.

With reference to FIG. 10H, processes 1 to 3 are always performed when the state is to be shifted from "wait" to "measure" upon any of the conditions in FIG. 10F being satisfied. Processes 1 to 3 in FIG. 10H are the same as processes 1 to 3 in FIG. 10G.

Figure 11:
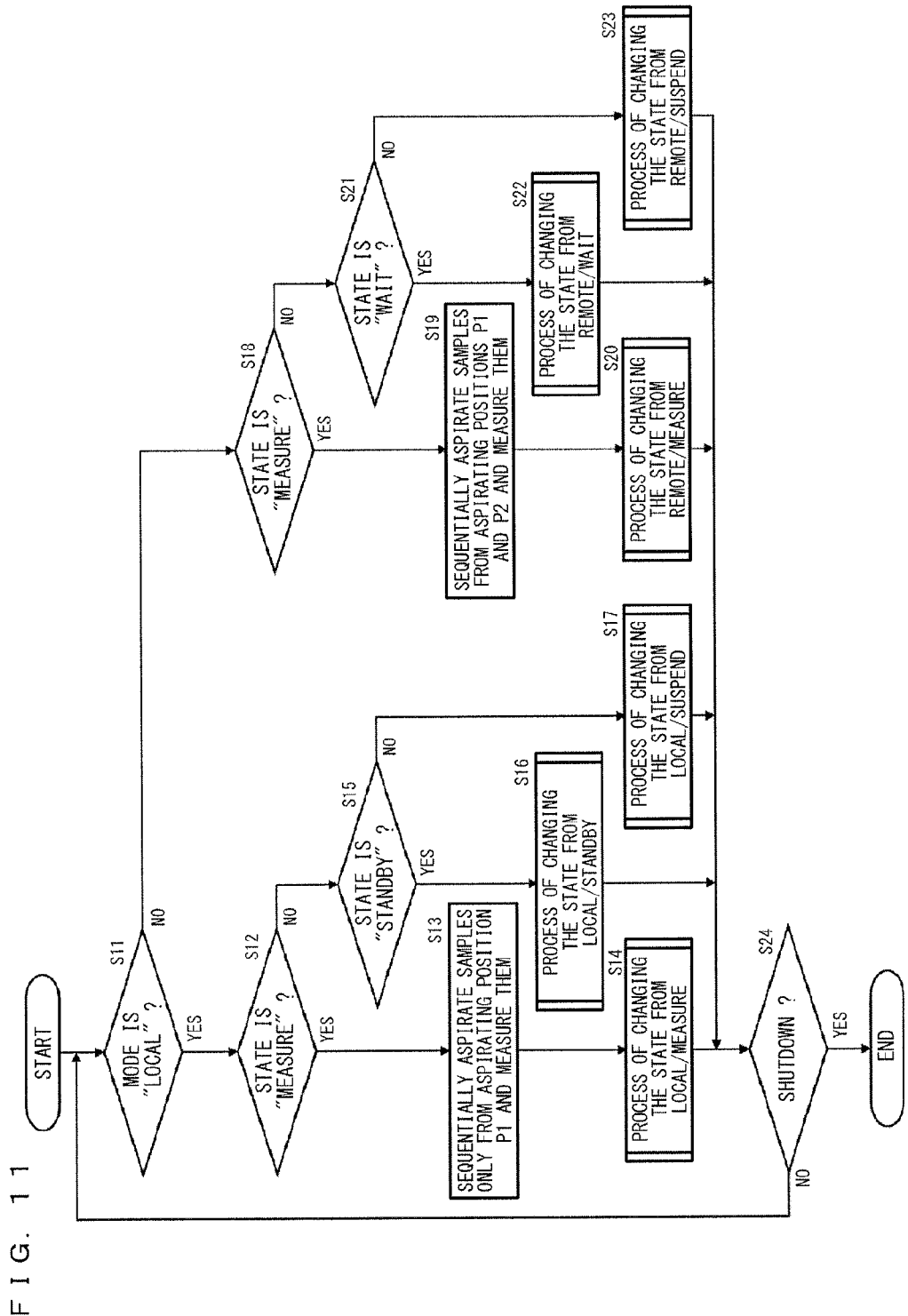
FIG. 11 is a flow chart showing processing performed by an information processing apparatus according to an embodiment.

FIG. 11 is a flow chart showing processing performed by the information processing apparatus 3.

Processing indicated by the flow chart in FIG. 11 is started when power supply to the measurement apparatus 2 is turned on. When power supply to the measurement apparatus 2 is turned on, the mode of the sample analyzer 1 becomes "local changeable", and the state becomes "standby". At this time, the body cover C1 and the diluent cover C3 are in unlocked states.

The CPU 301 of the information processing apparatus 3 determines whether the mode of the sample analyzer 1 is "local", based on the mode stored in the hard disk 304 (S11). When the mode is "local" (S11: YES), and when the mode is "remote" (S11: NO), the CPU 301 determines the state of the sample analyzer 1, based on the state stored in the hard disk 304 (S12, 515, 518, and S21). Then, as shown below, the CPU 301 performs processes in accordance with the mode and the state of the sample analyzer 1 and repeats the processes of S11 to S23 until a shutdown instruction is issued (S24).

When the mode of the sample analyzer 1 is "local" (S11: YES) and the state thereof is "measure" (S12: YES), the CPU 301 controls the measurement apparatus 2 so as to sequentially aspirate samples only from sample containers T each located at the aspirating position P1 and perform measurement on them (S13). Subsequently, the CPU 301 performs a "process of changing the state from local/measure" (S14). The "process of changing the state from local/measure" will be described later with reference to FIG. 12A.

When the mode of the sample analyzer 1 is "local" (S11: YES) and the state thereof is "standby" (S12: N0, S15: YES), the CPU 301 performs a "process of changing the state from local/standby" (S16). The "process of changing the state from local/standby" will be described later with reference to FIG. 13A.

When the mode of the sample analyzer 1 is "local" (S11: YES) and the state thereof is "suspend" (S12: N0, S15: NO), the CPU 301 performs a "process of changing the state from local/suspend" (S17). The "process of changing the state from local/suspend" will be described later with reference to FIG. 15A.

When the mode of the sample analyzer 1 is "remote" (S11: NO) and the state thereof is "measure" (S18: YES), the CPU 301 controls the measurement apparatus 2 so as to sequentially aspirate samples from sample containers T located at the aspirating positions P1 and P2 and perform measurement on them (S19). It should be noted that the CPU 301 causes the sample in the sample container T located at the aspirating position P2 to be aspirated, based on a command which indicates that a sample container T is located at the aspirating position P2 and which has been transmitted from the transportation controller 120. Subsequently, the CPU 301 performs a "process of changing the state from remote/measure" (S20). The "process of changing the state from remote/measure" will be described later with reference to FIG. 12B.

When the mode of the sample analyzer 1 is "remote" (S11: NO) and the state thereof is "wait" (S18: N0, S21: YES), the CPU 301 performs a "process of changing the state from remote/wait" (S22). The "process of changing the state from remote/wait" will be described later with reference to FIG. 13B.

When the mode of the sample analyzer 1 is "remote" (S11: NO) and the state is "suspend" (S18: N0, S21: NO), the CPU 301 performs a "process of changing the state from remote/suspend" (S23). The "process of changing the state from remote/suspend" will be described later with reference to FIG. 15B.

Figure 12A:
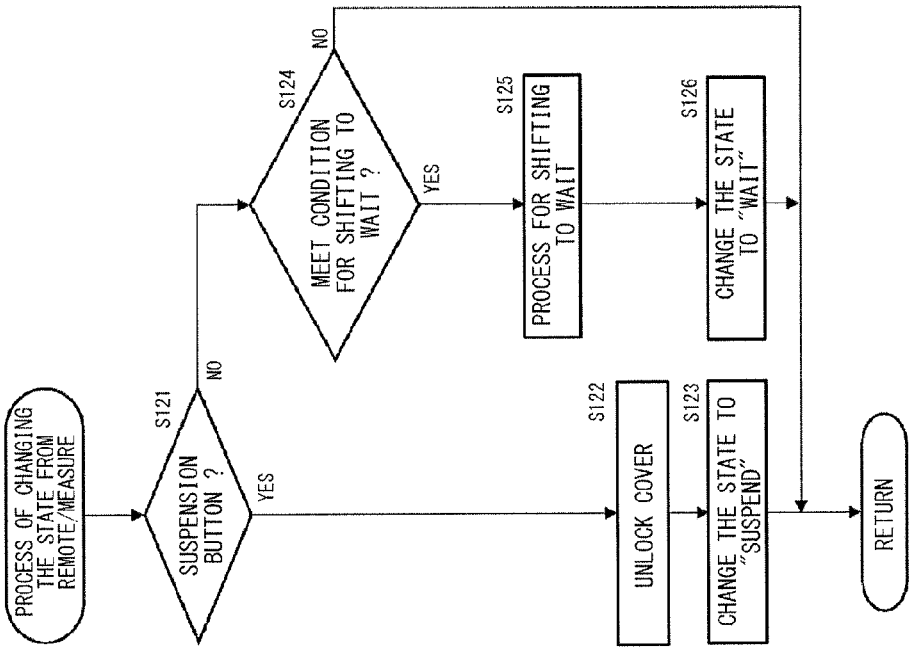
FIG. 12A is a flow chart showing a "process of changing the state from local/measure" according to an embodiment.

FIG. 12A is a flow chart showing the "process of changing the state from local/measure".

It should be noted that, in the description below, when the mode and the state of the sample analyzer 1 are to be changed, the CPU 301 changes the mode and the state stored in the hard disk 304 and transmits the changed mode and state to the transportation controller 120. Further, as described above, also when the reagent information button A21 has been pressed by the user and an instruction to replace a reagent container has been inputted via a reagent information screen (not shown), it is determined that the suspension button A12 has been pressed.

The CPU 301 of the information processing apparatus 3 determines whether the suspension button A12 has been pressed by the user (S111). When the suspension button A12 has been pressed (S111: YES), the CPU 301 unlocks the body cover C1 (S112), and changes the state to "suspend" (S113).

In addition to determining whether the suspension button A12 has been pressed, the CPU 301 determines whether the status of the sample analyzer 1 meets the "condition for shifting to standby" shown in FIG. 10A (S114). When the status of the sample analyzer 1 meets the "condition for shifting to standby" (S114: YES), the CPU 301 performs the "process for shifting to standby" shown in FIG. 10C (S115), unlocks the body cover C1 (S116), and changes the state to "standby" (S117).

Figure 12B:
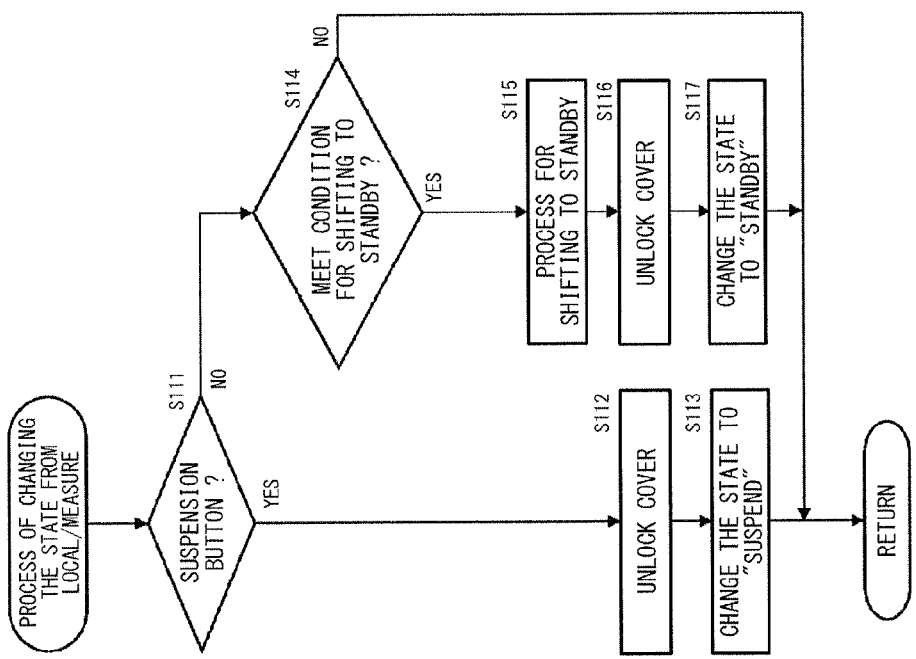
FIG. 12B is a flow chart showing a "process of changing the state from remote/measure"

FIG. 12B is a flow chart showing the "process of changing the state from remote/measure".

The CPU 301 of the information processing apparatus 3 determines whether the suspension button A12 has been pressed by the user (S121). When the suspension button A12 has been pressed (S121: YES), the CPU 301 unlocks the body cover C1 (S122), and changes the state to "suspend" (S123).

In addition to determining whether the suspension button A12 has been pressed, the CPU 301 determines whether the status of the sample analyzer 1 meets the "condition for shifting to wait" shown in FIG. 10B (S124). When the status of the sample analyzer 1 meets the "condition for shifting to wait" (S124: YES), the CPU 301 performs the "process for shifting to wait" shown in FIG. 10D (S125) and changes the state to "wait" (S126).

Figure 13B:
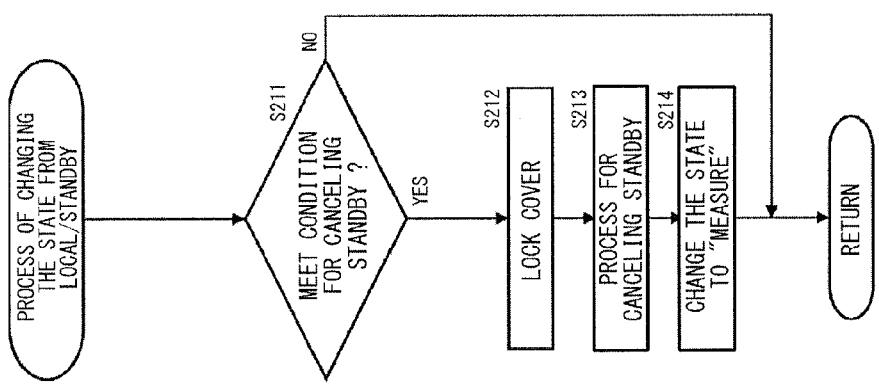
FIG. 13B is a flow chart showing a "process of changing the state from remote/wait"
Figure 13A:
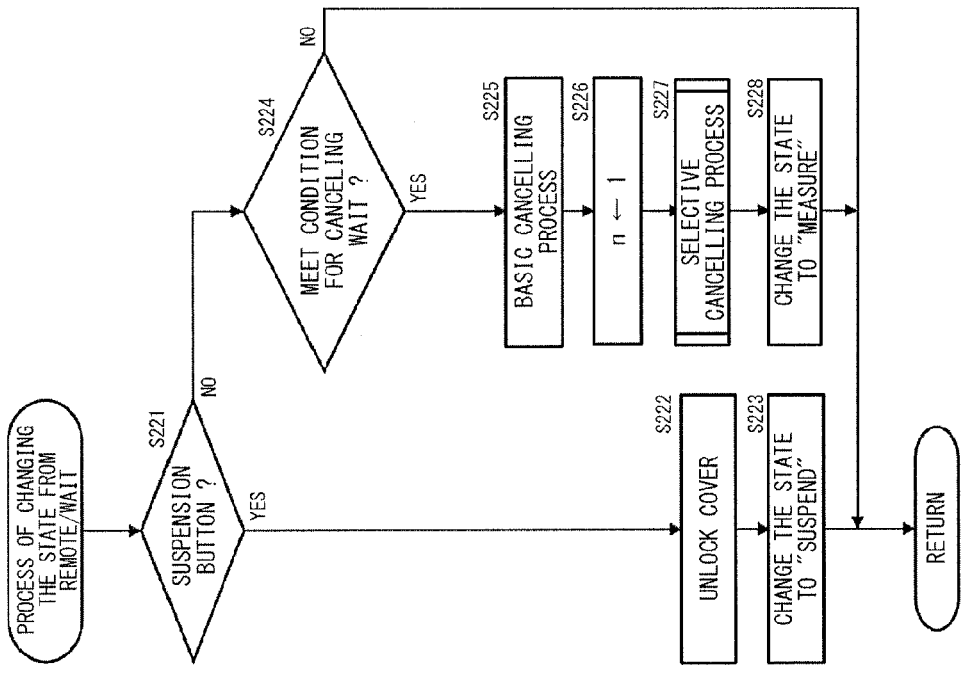
FIG. 13A is a flow chart showing a "process of changing the state from local/standby" according to an embodiment.

FIG. 13A is a flow chart showing the "process of changing the state from local/standby".

The CPU 301 of the information processing apparatus 3 determines whether the status of the sample analyzer 1 meets the "condition for canceling standby" shown in FIG. 10E (S211). When the status of the sample analyzer 1 meets the "condition for canceling standby" (S211: YES), the CPU 301 locks the body cover C1 (S212), performs the "process for canceling standby" shown in FIG. 10G (S213), and changes the state to "measure" (S214).

FIG. 13B is a flow chart showing the "process of changing the state from remote/wait".

The CPU 301 of the information processing apparatus 3 determines whether the suspension button A12 has been pressed (S221). When the suspension button A12 has been pressed (S221: YES), the CPU 301 unlocks the body cover C1 (S222), and changes the state to "suspend" (S223).

In addition to determining whether the suspension button A12 has been pressed, the CPU 301 determines whether the status of the sample analyzer 1 meets the "condition for canceling wait" shown in FIG. 10F (S224). When the status of the sample analyzer 1 meets the "condition for canceling wait" (S224: YES), the CPU 301 performs the basic cancelling process shown in FIG. 10H (S225). Subsequently, the CPU 301 sets 1 as a variable n stored in the hard disk 304 (S226). Then, the CPU 301 performs a "selective cancelling process" in which only a necessary process is performed using the variable n (S227), and then changes the state to "measure" (S228). The "selective cancelling process" will be described with reference to FIGS. 14A and 14B.

FIG. 14A illustrates the content of the "selective cancelling process".

For the item "target mechanism", mechanisms respectively assigned with numbers 1 to 9 are shown. For the item "confirmation content", confirmation contents corresponding to the nine target mechanisms are shown. For the item "processing content", processing contents corresponding to the nine target mechanisms are shown.

FIG. 14B is a flow chart showing the "selective cancelling process".

Based on a variable n set in advance, the CPU 301 of the information processing apparatus 3 determines whether the status of the nth target mechanism in FIG. 14A agrees with its corresponding confirmation content (S51). When the status of this target mechanism agrees with the confirmation content (S51: YES), the CPU 301 performs the processing content corresponding to this target mechanism (S52). On the other hand, when the status of this target mechanism does not agree with the confirmation content (S51: NO), the process proceeds to S53.

It should be noted that, with respect to the first target mechanism, i.e., the reagent tables 11 and 12, if one of the reagent tables has been moved, it is determined that the reagent tables 11 and 12 have been moved. Whether a target mechanism has been moved is determined based on pulse signals outputted from a rotary encoder that corresponds to a stepping motor that drives the target mechanism.

Subsequently, the CPU 301 increments the value of the variable n by 1 (S53), and determines whether the value of the variable n is greater than 9 (S54). When the value of the variable n is smaller than or equal to 9 (S54: NO), the process is returned to S51, and when the value of the variable n is greater than 9 (S54: YES), the process ends. In this manner, in the "selective cancelling process", an initialization process is performed only for a target mechanism, among all the target mechanisms shown in FIG. 14A, that requires initialization, and an initialization process is not performed for a target mechanism that does not require initialization.

Figure 15B:
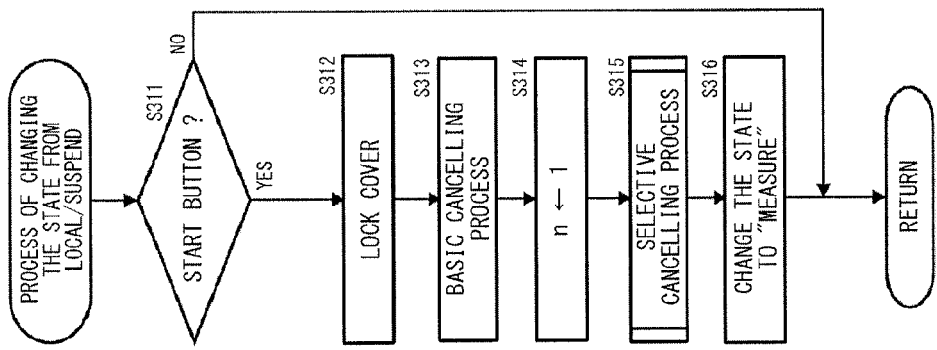
FIG. 15B is a flow chart showing a "process of changing the state from remote/suspend"
Figure 15A:
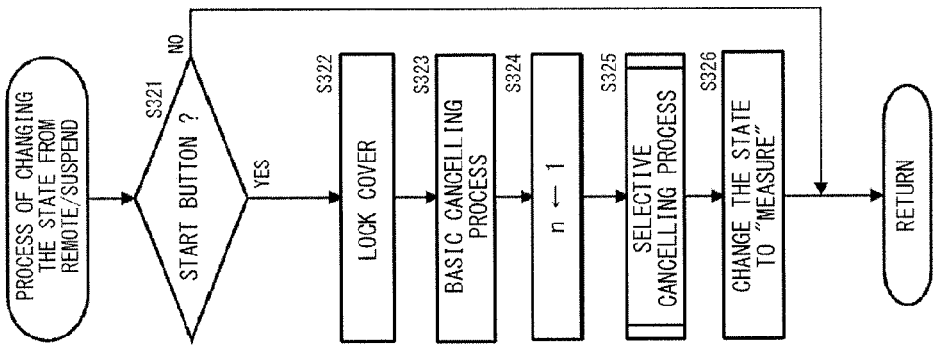
FIG. 15A is a flow chart showing a "process of changing the state from local/suspend" according to an embodiment.

FIG. 15A is a flow chart showing the "process of changing the state from local/suspend".

The CPU 301 of the information processing apparatus 3 determines whether the start button A11 has been pressed (S311). When the start button A11 has been pressed (S311: YES), the CPU 301 locks the body cover C1 (S312). Subsequently, the CPU 301 performs the basic cancelling process as in S225 to S228 in FIG. 13B (S313), sets 1 as the variable n (S314), and performs the "selective cancelling process" (S315). Then, the CPU 301 changes the state to "measure" (S316).

When the start button A11 has not been pressed (S311: NO), the CPU 301 ends the "process of changing the state from local/suspend" without performing processes.

FIG. 15B is a flow chart showing the "process of changing the state from remote/suspend".

The CPU 301 of the information processing apparatus 3 determines whether the start button A11 has been pressed (S321). When the start button A11 has been pressed (S321: YES), the CPU 301 performs processes similar to those of S312 to S316 in FIG. 15A (S322 to S326).

When the start button A11 has not been pressed (S321: NO), the CPU 301 ends the "process of changing the state from remote/suspend" without performing processes.

Figure 16:
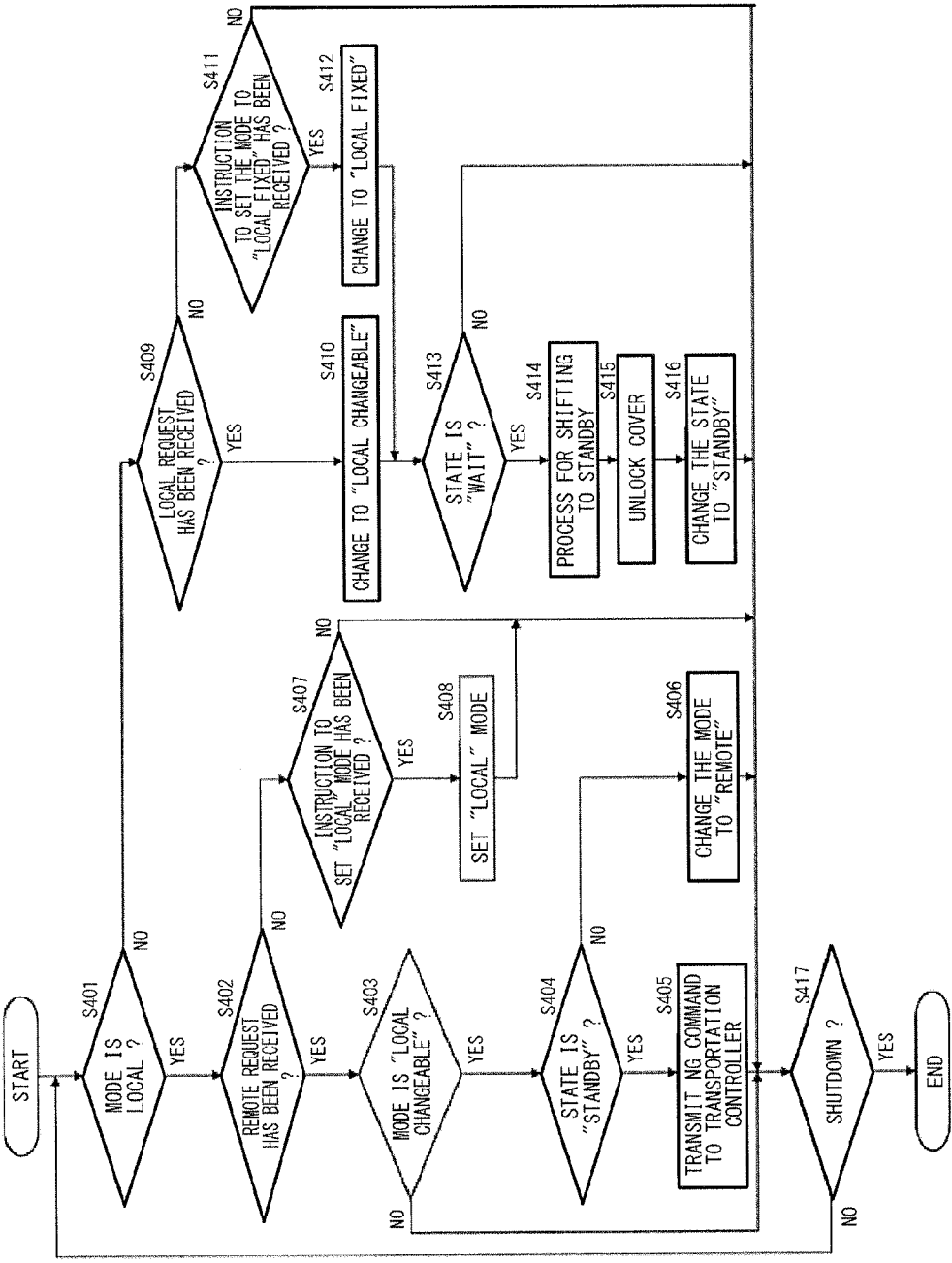
FIG. 16 is a flow chart showing how modes are changed by an information processing apparatus according to an embodiment.

FIG. 16 is a flow chart showing how modes are changed by the information processing apparatus 3.

Processing indicated by the flow chart in FIG. 16 is started when power supply to the measurement apparatus 2 is turned on. When power supply to the measurement apparatus 2 is turned on, the mode of the sample analyzer 1 automatically becomes "local changeable".

When the mode of the sample analyzer 1 is "local" (S401: YES), the CPU 301 of the information processing apparatus 3 determines whether a remote request (a command indicating that a sample container T has arrived at the bar code reader B, and the sample ID thereof read by the bar code reader B) has been received from the transportation controller 120 (S402). When the remote request has been received (S402: YES), the CPU 301 determines whether the mode is "local changeable" (S403).

When the mode is "local changeable" (S403: YES), the CPU 301 determines whether the state is "standby" (S404). When the mode is "local fixed" (S403: NO), the process proceeds to S417.

When the state is "standby" (S404: YES), the CPU 301 transmits to the transportation controller 120 an NG command which indicates that the mode of the sample analyzer 1 cannot be changed to "remote" (i.e., the sample on the transportation line Ln cannot be received) (S405). On the other hand, when the state is not "standby" (S404: NO), the CPU 301 changes the mode to "remote" (S406). That is, when the mode is "local" and the state is "measure", the mode is changed to "remote" and the state is set to "measure"; and when the mode is "local" and the state is "suspend", the mode is changed to "remote" and the state is set to "suspend".

Meanwhile, when a remote request has not been received from the transportation controller 120 (S402: NO), the CPU 301 determines whether the user has issued an instruction to set the mode to "local" (S407). Such an instruction is issued by pressing the OK button on the local mode changing screen A32 shown in FIG. 8B. When the checkbox A32a is checked and the OK button is pressed, the CPU 301 sets the mode to "local fixed", and when the checkbox A32a is unchecked and the OK button is pressed, the CPU 301 sets the mode to "local changeable" (S408).

Meanwhile, when the mode is "remote" (S401: NO), the CPU 301 determines whether a local request (a notification indicating that there is no more sample container to be transported to the container storing apparatus 103 and that the transportation line Ln is to be stopped) has been received from the transportation controller 120 (S409). When the local request has been received (S409: YES), the CPU 301 changes the mode to "local changeable" (S410). At this time, the state that has been set for "remote" is maintained.

On the other hand, when the local request has not been received (S409: NO), the CPU 301 determines whether the user has issued an instruction to set the mode to "local fixed" (S411). Such an instruction is issued when the unchecked checkbox A32a on the local mode changing screen A32 shown in FIG. 8B is checked and the OK button is pressed. When the instruction to set the mode to "local fixed" is issued (S411: YES), the CPU 301 changes the mode to "local fixed" (S412). At this time, the state that has been set for "remote" is maintained.

Subsequently, when the state is "wait" (S413: YES), the CPU 301 performs the "process for shifting to standby" shown in FIG. 10C (S414), unlocks the body cover C1 (S415), and changes the state to "standby" (S416). On the other hand, when the state is not "wait" (S413: NO), the process proceeds to S417.

In this manner, until a shutdown instruction is issued, the CPU 301 repeats the processes of S401 to S416 (S417).

As described above, according to the present embodiment, as shown in S124 and thereafter in FIG. 12B, in the case where the mode is "remote" and the state is "measure", even if the status of the sample analyzer 1 meets the "condition for shifting to wait", the body cover C1 is kept locked. Accordingly, when the mode is "remote" and the state is "wait", the moving mechanism group in the body cover C1 cannot be displaced by the user. This eliminates the necessity to set all the moving mechanisms included in the moving mechanism group to their original positions every time a sample container T is transported along the transportation line Ln of the transportation unit 114 and the state is changed from "wait" to "measure". Thus, it is possible to prevent delay of measurement.

More specifically, when performing measurement using the transportation unit 50 (dedicated transporting apparatus), the user usually sets a plurality of sample racks L in the transportation unit 50 at one time to perform measurement. Therefore, the measurement state is maintained, without the sample analyzer 1 entering the standby state between operations for the plurality of sample racks L that have been set at one time. On the other hand, when performing measurement using the transportation line Ln, samples are transported from another apparatus one by one with an interval therebetween, which causes increased opportunities for the sample analyzer 1 to enter the wait state in time intervals between the samples. If the body cover C1 is unlocked every time the sample analyzer 1 enters the wait state, moving mechanisms need to be returned to their original positions for every next sample measurement, which causes delay of measurement. However, in the present embodiment, by keeping the body cover C1 locked, moving mechanisms need not be returned to their original positions, and thus measurement can be performed without delay.

Further, in the case where measurement ends while the mode is "local", and the state is shifted to "standby", the body cover C1 is automatically unlocked. This eliminates the necessity for the user to perform an operation to unlock the body cover C1, and thus, the operations performed by the user can be simplified. Accordingly, it is possible to smoothly perform replacement of reagents and the like.

Further, according to the present embodiment, as shown in S224 and thereafter in FIG. 13B, when the mode is "remote" and the state is "wait", the locked body cover C1 is unlocked when the suspension button A12 is pressed by the user. Accordingly, even when the state is "wait", the user can unlock the body cover C1 as necessary.

Further, according to the present embodiment, as shown in S114 and thereafter in FIG. 12A, when the mode is "local" and the state is "measure", if the status of the sample analyzer 1 meets the "condition for shifting to standby", the body cover C1 is unlocked. Accordingly, when all measurements have ended for the sample containers T in the sample racks L set in the rack set region 51 of the transportation unit 50, the body cover C1 is unlocked. Thus, after the measurements end, the user need not perform an operation to unlock the body cover C1 for reagent replacement or maintenance, and thus operations performed by the user can be simplified.

Further, according to the present embodiment, when the mode is "remote" and the state is "wait", if the mode is changed to "local" in S410 or S412 in FIG. 16, the body cover C1 is unlocked as shown in S415 in FIG. 16. Accordingly, after the mode has been switched from "remote" to "local", the user need not perform an operation to unlock the body cover C1, and thus, operations performed by the user can be simplified.

Further, according to the present embodiment, as shown in S124 and thereafter in FIG. 12B, when the mode is "remote" and the state is "measure", if the status of the sample analyzer 1 meets the "condition for shifting to wait", the "process for shifting to wait" including a process of turning off the drive of the pneumatic source 213 is performed. Accordingly, when the state becomes "wait", it is possible to suppress power used by the sample analyzer 1 to a low level, and it is possible to suppress degradation of the pneumatic source 213.

Although the embodiment of the present invention has been described as above, the present invention is not limited to the above embodiment, and various modifications of the above embodiment may be made.

For example, in the above embodiment, the sample analyzer 1 is implemented by a blood coagulation analyzer. However, the present invention is not limited thereto, and the sample analyzer 1 may be any type of sample analyzer. For example, the sample analyzer 1 may be an immune analyzer that measures serum, a blood cell counter that counts the number of blood cells in blood, a urine analyzer that measures urine, or an analyzer that analyzes bone marrow fluid.

Further, in the present embodiment, an example in which the present invention is applied to the sample analyzer 1 has been described. However, the present invention is not limited to a sample analyzer that analyzes samples, and can be applied to a sample processing apparatus that performs a predetermined process on samples. For example, the present invention may be applied to a smear preparing apparatus that prepares smears, a centrifuge for centrifuging sample containers T, or a sample rearranging apparatus for rearranging sample containers T.

Further, in the above embodiment, the apparatuses located along the transportation line Ln of the transportation system 110 include the centrifuge 102 in addition to the sample analyzers 1. However, the present invention is not limited thereto, and other sample analyzers or other sample processing apparatuses may be included.

Further, in the above embodiment, in S226 and S227 in FIG. 13B, the processes are performed only for a target mechanism that requires initialization. However, the present invention is not limited thereto, and the process for initializing a target mechanism may be performed based on whether the body cover C1 has been unlocked.

Figure 17B:
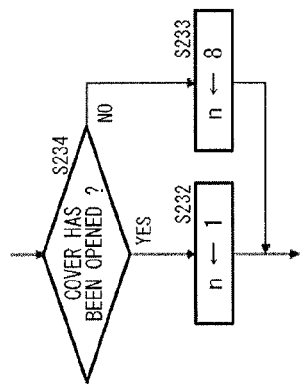
FIGS. 17A to 17C are flow charts each showing a "process of changing the state from remote/wait" according to a modification.
Figure 17C:
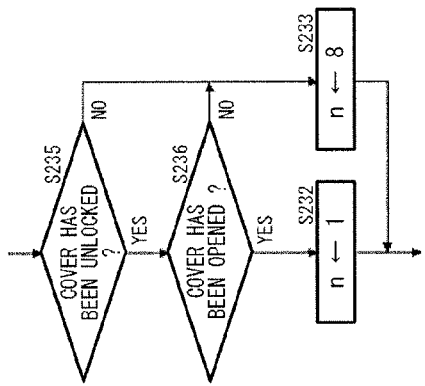
Figure 17A:
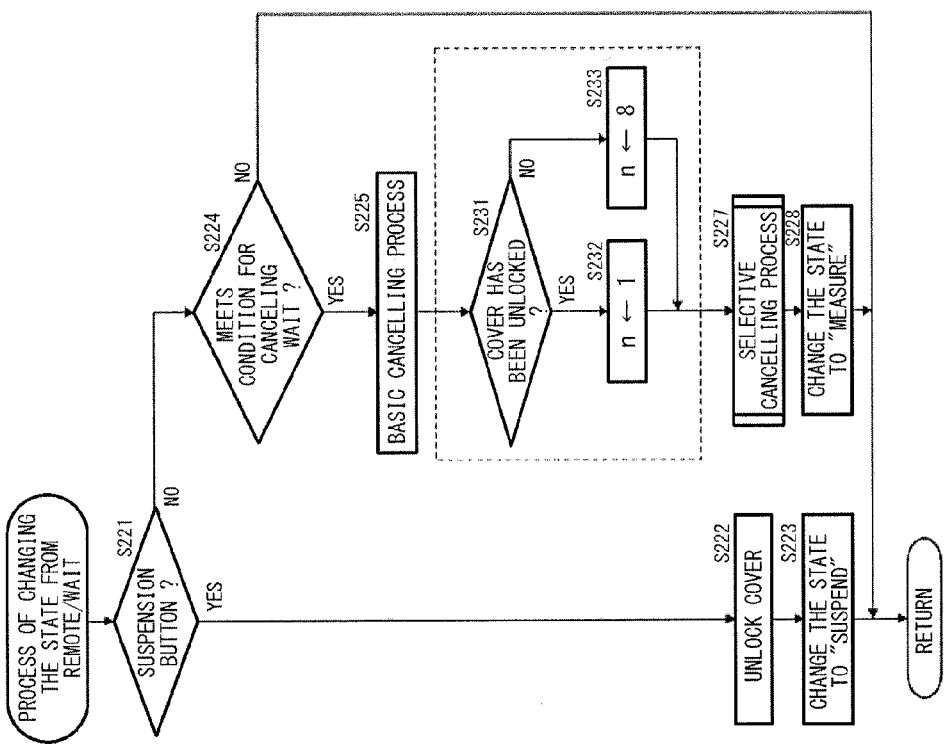

FIG. 17A is a flow chart showing a "remote/wait process" for this case. In FIG. 17A, processes of S231 to S233 are added instead of S226 in FIG. 13B. This part alone will be described below.

Since the state is "wait" when the process of S231 is started, the body cover C1 is usually locked. However, there is a possibility that the body cover C1 has been unlocked due to an error or the like during a period (hereinafter, referred to as "lock verification period") from when the state was changed from "measure" to "wait" to when the determination in S231 is started. When the body cover C1 has been unlocked in the lock verification period, there is a possibility that the positions of the mechanisms covered by the body cover C1 have been changed.

The CPU 301 of the information processing apparatus 3 determines whether the body cover C1 has been unlocked during the lock verification period (S231). When the body cover C1 has been unlocked during the lock verification period (C231: YES), the CPU 301 sets 1 as the variable n (S232). Then, initialization processes for the target mechanisms numbered 1 to 9 shown in FIG. 14A are performed (S227). Whether the body cover C1 has been unlocked is determined by whether the motor C24 shown in FIGS. 4A and 4B has been operated during the lock verification period. Alternatively, a switch may be provided that is turned on when the engaging plate C22 is shifted from the state of FIG. 4B to the state of FIG. 4A, and whether the body cover C1 has been unlocked may be determined by monitoring an output from this switch.

On the other hand, when the body cover C1 has been kept locked during the lock verification period (C231: NO), the CPU 301 sets 8 as the variable n (S233). Then, initialization processes are performed only for the target mechanisms numbered 8 and 9 shown in FIG. 14A (S227). Accordingly, when the body cover C1 has been kept locked and there is no possibility that the positions of the mechanisms covered by the body cover C1 have been changed, initialization processes are not performed for the target mechanisms numbered 1 to 7 which are covered by the body cover C1. Accordingly, since some moving mechanisms included in the moving mechanism group covered by the body cover C1 are not returned to their original positions, it is possible to prevent delay of measurement.

In FIG. 17A, initialization processes for target mechanisms are performed based on whether the body cover C1 is unlocked. Alternatively, initialization processes for target mechanisms may be performed based on whether the body cover C1 has been actually opened by the user. In this case, a sensor is provided, near the lock mechanism C2, that can determine whether the body cover C1 is in a closed state or an opened state, and whether the body cover C1 has been actually opened or not is determined by the sensor.

FIG. 17B is a portion of a flow chart indicating the process performed in this case. In FIG. 17B, a process S234 is added instead of S231 in FIG. 17A. Also in this case, when the body cover C1 has not been opened (S234: NO), some moving mechanisms included in the moving mechanism group covered by the body cover C1 are not returned to their original positions, and thus, it is possible to prevent delay of measurement.

Further, initialization processes for target mechanisms may be performed based on whether the body cover C1 has been unlocked, and on whether the body cover C1 has been actually opened by the user.

FIG. 17C is a portion of a flow chart indicating the process in this case. In FIG. 17C, processes of S235 and S236 are added instead of S231 in FIG. 17A. In this case, only when the body cover C1 has been unlocked and the body cover C1 has been opened (S235: YES, S236: YES), initialization processes are performed for the target mechanisms numbered 1 to 9 shown in FIG. 14A. In other cases than this, since some moving mechanisms included in the moving mechanism group covered by the body cover C1 are not returned to their original positions, it is possible to prevent delay of measurement.

In addition to the above, various modifications of the embodiment of the present invention may be made as appropriate without departing from the scope of the technical idea defined by the claims.

What is claimed is:

1. A sample processing apparatus for processing a sample, comprising:
   a sample processing unit comprising a moving mechanism and configured to perform a sample processing operation by moving the moving mechanism;
   a cover configured to cover the moving mechanism of the sample processing unit;
   a lock mechanism configured to lock the cover to prevent the cover from being opened;
   a non-transitory memory configured to store information of a mode that is set between a first mode and a second mode;
   a processor programmed to execute a computer program that enables the processor to:
   control the lock mechanism to keep the cover locked after the sample processing unit has completed the sample processing operation until an instruction to unlock the cover is received from a user when the first mode is set; and
   control the lock mechanism to unlock the cover after the sample processing unit has completed the sample processing operation when the second mode is set.

2. The sample processing apparatus according to claim 1, wherein
   the sample processing unit is arranged adjacently to a transportation line which transports a sample to the sample processing unit and another sample processing unit, and
   the processor is further programmed to set the first mode when the sample processing unit processes the sample transported by the transportation line by moving the moving mechanism.

3. The sample processing apparatus according to claim 2, further comprising:
   a dedicated transportation unit which transports a sample only to the sample processing unit, and
   the processor is further programmed to set the second mode when the sample processing unit processes not the sample transported by the transportation line but the sample transported by the dedicated transportation unit by moving the moving mechanism.

4. The sample processing apparatus according to claim 3, wherein
   when the first mode is set, the sample processing unit is configured to process the sample transported by the dedicated transportation unit in addition to the sample transported by the transportation line by moving the moving mechanism.

5. The sample processing apparatus according to claim 3, wherein
   when the second mode is set, the processor further programmed to lock the cover upon receiving from the user an instruction to start an operation of processing a sample set in the dedicated transporting apparatus.

6. The sample processing apparatus according to claim 3, wherein
   the dedicated transporting apparatus is configured to transport a sample rack for accommodating a plurality of sample containers to the sample processing unit, and
   the transportation line is configured to individually transport a holder for holding one sample container to the sample processing unit.

7. The sample processing apparatus according to claim 5, wherein
   when having shifted the mode of the sample processing apparatus to the first mode while the cover has been locked, the processor is further programmed to keep the cover locked until receiving from the user an instruction to unlock the cover.

8. The sample processing apparatus according to claim 1, wherein
   when the first mode is switched to the second mode while the cover is kept locked after the sample processing operation has been completed in the first mode, the processor is further programmed to unlock the cover.

9. The sample processing apparatus according to claim 2, wherein
   when the sample transported by the transportation line arrives at the sample processing unit while the second mode is set, the processor is further programmed to switch the second mode to the first mode.

10. The sample processing apparatus according to claim 9, wherein
    when the processor has determined that there is no sample on the transportation line while the first mode is set, the processor is further programmed to switch the first mode to the second mode.

11. The sample processing apparatus according to claim 1, wherein
when the first mode is set, the controller shifts the mode of the sample processing apparatus to a power saving mode after the sample processing operation has been completed, and the processor is further programmed to keep the cover locked after the power saving mode has been set until an instruction to unlock the cover is received from the user.

12. The sample processing apparatus according to claim 11, wherein
the sample processing unit comprises a pressure source configured to generate a pressure for sample processing, and
the processor is further programmed to stop operation of the pressure source in the power saving mode.

13. The sample processing apparatus according to claim 1, wherein
the processor is further programmed to unlock the cover upon receiving an instruction for replacing a reagent.

14. The sample processing apparatus according to claim 1, wherein
the processor is further programmed to control the sample processing unit to start the sample processing operation without returning the moving mechanism covered by the cover to an original position if the cover has not been opened during a period between when the sample processing operation was completed and when the sample processing operation is resumed.

15. The sample processing apparatus according to claim 1, wherein
the processor is further programmed to control the sample processing unit to start the sample processing operation without returning the moving mechanism covered by the cover to an original position if the cover has been kept locked during a period between when the sample processing operation was completed and when the sample processing operation is resumed.

16. The sample processing apparatus according to claim 1, wherein
the moving mechanism includes at least one of: a reagent accommodation mechanism which comprises an accommodation part configured to accommodate a reagent container containing a reagent to be used in sample processing, and the processor is further programmed to control the moving mechanism to move the accommodation part and to control a reagent dispensing mechanism to perform a reagent dispensing operation.

\* \* \* \* \*